(12) United States Patent
Wang et al.

(10) Patent No.: US 10,371,656 B2
(45) Date of Patent: Aug. 6, 2019

(54) TOMOGRAPHY APPARATUS AND METHOD

(71) Applicant: UNIVERSITY OF LEEDS, Leeds, Yorkshire (GB)

(72) Inventors: Mi Wang, Leeds (GB); Bishal Karki, Leeds (GB); Qiang Wang, Leeds (GB)

(73) Assignee: UNIVERSITY OF LEEDS, Leeds, Yorkshire (GB)

( * ) Notice: Subject to any disclaimer, the term of this patent is extended or adjusted under 35 U.S.C. 154(b) by 93 days.

(21) Appl. No.: 15/511,132

(22) PCT Filed: Sep. 15, 2015

(86) PCT No.: PCT/GB2015/052671
§ 371 (c)(1),
(2) Date: Mar. 14, 2017

(87) PCT Pub. No.: WO2016/042316
PCT Pub. Date: Mar. 24, 2016

(65) Prior Publication Data
US 2017/0254765 A1   Sep. 7, 2017

(30) Foreign Application Priority Data

Sep. 15, 2014 (GB) .................................. 1416280.4

(51) Int. Cl.
*G01N 27/20* (2006.01)
*G01N 27/02* (2006.01)

(52) U.S. Cl.
CPC .................................. *G01N 27/026* (2013.01)

(58) Field of Classification Search
CPC ...... G01N 27/06; G01N 27/041; G01N 27/20; G01N 27/07; G01N 27/02; G01N 33/66; G01N 5/00

(Continued)

(56) References Cited

U.S. PATENT DOCUMENTS

| | | | | |
|---|---|---|---|---|
| 4,707,658 A | * | 11/1987 | Frahm | .................. G01R 33/482 324/309 |
| 5,807,251 A | | 9/1998 | Wang et al. | |

(Continued)

FOREIGN PATENT DOCUMENTS

| CN | 201476825 U | 5/2010 |
|---|---|---|
| CN | 102435637 A | 5/2012 |

(Continued)

OTHER PUBLICATIONS

Giguere (Characterization of slurry flow regime transitions by ERT, Chemical Engineering Research and Design Part A vol. 86, No. 9.1 Sep. 2008, pp. 989-996, XP023980366JSSN: 0263-8762, DOI: 10.1016/J.CHERD.2008.03.014).*

(Continued)

*Primary Examiner* — Jermele M Hollington
*Assistant Examiner* — Taqi R Nasir
(74) *Attorney, Agent, or Firm* — Patterson, Thuente, Pedersen, P.A.

(57) ABSTRACT

Tomography apparatus comprises: a plurality of electrodes arranged around a perimeter of a cross section of a sample volume for containing a liquid or mixed-phase sample, each electrode being arranged to be in electrical contact with a sample contained in the sample volume; measurement means adapted to perform a set of measurements, each measurement comprising driving a current between a first respective adjacent pair of said electrodes and measuring a voltage developed across a second respective adjacent pair of said electrodes; and processing means adapted to generate a tomogram indicative of sample conductivity over said cross section from said set of measurements. The processing means is arranged to calculate sample conductivity values of a portion of said cross section from said set of measurements and generate said tomogram from said calculated sample (Continued)

conductivity values of said portion using an assumption of symmetry.

19 Claims, 11 Drawing Sheets

(58) Field of Classification Search
USPC ....... 324/316, 347, 693, 358, 359, 370, 447, 324/448, 449, 250, 515, 754.22
See application file for complete search history.

(56) References Cited

U.S. PATENT DOCUMENTS

| | | | |
|---|---|---|---|
| 6,940,286 | B2 | 9/2005 | Wang et al. |
| 2011/0166814 | A1* | 7/2011 | Mahalingam .......... G01N 27/02 702/77 |
| 2012/0235693 | A1* | 9/2012 | Feng ...................... G01N 27/20 324/693 |
| 2012/0262176 | A1* | 10/2012 | Czechowski .......... G01N 24/10 324/316 |
| 2013/0049770 | A1* | 2/2013 | Basu ..................... G01N 27/026 324/654 |
| 2015/0097589 | A1* | 4/2015 | Orazem ................. G01N 17/04 324/693 |
| 2015/0145532 | A1* | 5/2015 | Kersey .................. G01N 17/02 324/663 |

FOREIGN PATENT DOCUMENTS

| | | |
|---|---|---|
| CN | 102597755 A | 7/2012 |
| EP | 2343538 A2 | 7/2011 |
| EP | 2418478 A1 | 10/2016 |
| WO | WO 2002/053029 A1 | 7/2002 |
| WO | WO 2009/030870 A1 | 3/2009 |
| WO | WO 2010/150009 A1 | 12/2010 |
| WO | WO 2011/128656 A1 | 10/2011 |

OTHER PUBLICATIONS

PCT International Search Report and Written Opinion for PCT/GB2015/052671 dated Nov. 30, 2015, 15 pages.

Giguere R et al: "Characterization of slurry flow regime transitions by ERT", Chemical Engineering Research and Design, Part A, Institution of Chemical Engineers, XX, vol. 86, No. 9, Sep. 1, 2008 (Sep. 1, 2008), pp. 989-996, XP023980366, ISSN: 0263-8762, DOI: 10.1016/J.CHERD.2008.03.014 [retrieved on May 22, 2008].

Zdzislaw Szczepanik et al: "Frequency Analysis of Electrical Impedance Tomography System", IEEE Transactions on Instrumentation and Measurement, IEEE Service Center, Piscataway, NJ, US, vol. 49, No. 4, Aug. 1, 2000 (Aug. 1, 2000), XP011025064, ISSN: 0018-9456.

Yi Li et al: "Gas/oil/water flow measurement by electrical capacitance tomography", Imaging Systems and Techniques (IST), 2012 IEEE International Conference on, IEEE, Jul. 16, 2012 (Jul. 16, 2012), pp. 83-88, XP032237187, DOI: 10.1109/IST.2012.6295481 ISBN: 978-1-4577-1776-5.

GB Application No. 1416280.4, Search Report dated Mar. 10, 2015, 4 pages.

U.S. Appl. No. 15/511,155, filed Mar. 14, 2017, Inventor(s): Wang et al.

PCT International Search Report and Written Opinion for PCT/GB2015/052672 dated Mar. 1, 2016 (19 pages).

Xiang Deng et al: "Fusion Research of Electrical Tomography with Other Sensors for Two-phase Flow Measurement", Measurement Science Review, vol. 12, No. 2, Jan. 1, 2012 (Jan. 1, 2012), pp. 62-67, XP055135675, ISSN: 1335-8871, DOI: 10.2478/v10048-012-0008-7.

Xiang Deng et al: "Theoretical study of vertical slug flow measurement by data fusion from electromagnetic flowmeter and electrical resistance tomography", Flow Measurement and Instrumentation, Butterworth-Heinemann, Oxford, GB, vol. 22, No. 4, Mar. 15, 2011 (Mar. 15, 2011), pp. 272-278, XP028224069, ISSN: 0955-5986, DOI: 10.1016/J.FLOWMEASINST.2011.03.007 [retrieved on Mar. 23, 2011].

Xiang Deng et al: "Study on fusion of electromagnetic flowmeter and ERT system in slug flow", 9th International Conference on Electronic Measurement & Instruments, 2009 : ICEMI '09 : Aug. 16-19, 2009, Beijing, China ; Proceedings, IEEE, Piscataway, NJ, USA, Aug. 16, 2009 (Aug. 16, 2009), pp. 1-365, XP031537858, ISBN: 978-1-4244-3863-1.

Search Report under Section 17(5) for UK Application No. 1416287.9, dated Mar. 17, 2015 (4 pages).

* cited by examiner

Initial Test Results
Sensitivity distributions

SBP          ASI

Stups (conventional SBP)

Three agar rods with diff. conductivity    Simulated one low conductive object    Simulated two low conductive objects Central rows show (conventional SBP)

Central rows show (ASI)

TOMOGRAPHY APPARATUS AND METHOD

RELATED APPLICATIONS

The present application is a National Phase entry of PCT Application No. PCT/GB2015/052671, filed Sep. 15, 2015, which claims priority from GB Patent Application No. 1416280.4, filed Sep. 15, 2014, said applications being hereby incorporated by reference herein in their entirety.

FIELD OF THE INVENTION

The present invention relates to tomography apparatus and corresponding tomography methods and in particular, although not exclusively, to apparatus and methods for producing tomograms of flowing samples, such as flowing mixtures of fluids, solids, gases, or combinations thereof (i.e. mixed-phase samples).

BACKGROUND TO THE INVENTION

A wide variety of tomography apparatus and methods are known, including systems based on electrical impedance tomography (EIT) and electrical resistance tomography (ERT). It is also known to use such apparatus and methods for generating tomograms (e.g. conductivity profiles of cross sections of samples) of substantially stationary samples and also for moving the samples, for example flowing samples in a pipe or other conduit, such as liquids, solids, gases or any combination or mixture thereof. In such applications an array of electrodes is typically arranged around the perimeter of a sample-containing volume, such that each electrode is in electrical contact with the sample. The apparatus then comprises measurement means which is adapted to perform a set of measurements on the sample, each measurement comprising the passing of a current through the sample using a pair of the electrodes, and measuring a resultant voltage developed across a different pair of the electrodes. In general, the larger the number of electrodes and the larger the number of different measurements made using those electrodes, the higher the resolution of the tomogram that can be calculated from the measurements. The apparatus typically comprises processing means adapted to calculate a tomogram representing the conductivity of the sample as a function of position on the cross section surrounded by the electrodes from the complete set of measurement results. The apparatus may also comprise display means adapted to display the calculated tomogram. The tomogram may comprise a plurality of pixels. The mathematical/processing techniques for generating tomograms from the measurement results/data are well known in the prior art, and will be apparent to the person skilled in this field.

In certain known tomography apparatus, 16 electrodes are equally spaced around a circular perimeter of a sample-containing volume, and the measurement means is adapted to take a set of measurements using the so-called "adjacent pair" technique. In the adjacent-pair method, each measurement comprises passing a current through the sample using one adjacent pair of electrodes, and measuring a resultant voltage developed across a different adjacent pair of electrodes. It is known for the data set to comprise 104 such measurements for an array of 16 electrodes, with this set comprising 8 sub-sets (or alternatively 16 sub-sets—see below), each sub-set using a different adjacent pair of electrodes to pass current through the sample and no electrode being used in more than one pair of exciting/current-driving pairs. Then, in each sub-set, with the selected adjacent pair of electrodes driving current through the sample, 13 different voltage measurements are made using the full set of different adjacent pairs of remaining electrodes (i.e. the electrodes other than the pair selected to drive current). For example, in a first sub-set, electrodes 1 and 2 may be used to drive current through the sample. Then, voltage measurements are taken between electrodes 3 and 4, 4 and 5, 5 and 6, etc. up to the final voltage measurement between electrodes 15 and 16. Thus, the electrodes 1 and 2 being used in this sub-set to drive current are not used in any of the corresponding voltage measurements, thereby avoiding any problems associated with electrode to sample impedances. Also, it is known for the initial data set obtained from an array of 16 electrodes to comprise 16 subsets, with a total of 256 measurements initially being made. Then, only 104 measurements may be used as independent measurements, by removing those measurements obtained from electrodes involved with current injection and measurements as the mutual same based on the reciprocity theory in electrical impedance measurement. These are determined by $N=(Ne-3)Ne/2$ or $104=(16-3)16/2$ (where Ne is the number of electrodes).

Whilst this known technique of deriving a tomogram from 104 measurements, or an even greater number, made using the set of 16 electrodes is able to produce tomograms with useful resolution, it will be appreciated that the amount of processing required to produce the tomogram is large. This places high demands on the processing apparatus required, and in general, of course, for a given processing capacity the larger the number of measurements and resultant processing operations to be performed to produce the tomogram, the longer the time taken to produce the tomogram.

SUMMARY OF THE INVENTION

It is an aim of certain embodiments of the invention to overcome, at least partly, at least one of the problems associated with the prior art.

It is an object of certain embodiments of the invention to provide tomography apparatus and corresponding methods able to produce tomograms of resolution better than, the same as, or comparable with prior art techniques from fewer measurements and/or with fewer processing operations than the prior art.

Certain embodiments of the invention aim to provide tomography apparatus producing high resolution tomograms quickly, and especially for use in the imaging of flowing samples (e.g. mixed phase samples).

According to a first aspect of the invention there is provided tomography apparatus comprising:

a plurality of electrodes arranged around a perimeter of a cross section of a sample volume for containing a liquid or mixed-phase sample, each electrode being arranged to be in electrical contact with a sample contained in the sample volume (in other words, each electrode comprises a respective contact surface arranged to be in electrical contact with a sample in the sample volume);

measurement means adapted to perform a set of measurements, each measurement comprising driving a current between a first respective adjacent pair of said electrodes and measuring a voltage developed across a second respective adjacent pair of said electrodes; and processing means adapted to generate a tomogram indicative of sample conductivity over said cross section from said set of measurements, characterised in that the processing means is arranged to calculate sample conductivity values of a portion of said cross section from said set of measurements and generate said tomogram from said calculated sample conductivity values of said portion using an assumption of symmetry.

In certain embodiments, the plurality of electrodes are distributed asymmetrically (or non-uniformly) around said perimeter.

In certain embodiments, said portion is one half of said cross section, and the assumption of symmetry is that sample conductivity over the other half mirrors said one half.

In certain embodiments, the apparatus further comprises a cylindrical pipe, arranged with its longitudinal axis horizontal, arranged to contain a flowing sample, the sample volume being an interior volume of the pipe, and said cross section being a circular cross section of the pipe interior, in a vertical plane perpendicular to the longitudinal axis.

In certain embodiments, said portion is a radial portion extending from a centre of the cross section to the perimeter, and the assumption of symmetry is that sample conductivity over said cross section is a function of radius only.

In certain embodiments, the apparatus further comprises a cylindrical pipe, arranged with its longitudinal axis vertical, arranged to contain a flowing sample, the sample volume being an interior volume of the pipe, and said cross section being a circular cross section of the pipe interior, in a horizontal plane.

In certain embodiments, said plurality of electrodes consists of 8 electrodes, said perimeter is circular, and 6 of said 8 electrodes are distributed around one half of the perimeter, with the remaining 2 of said 8 electrodes being distributed around the other half of the perimeter.

In certain embodiments, said plurality of electrodes are distributed uniformly around said perimeter.

In certain embodiments, said portion extends across the cross section from one side of the perimeter to an opposite side of the perimeter and includes a centre of the cross section.

In certain embodiments, said portion is a band extending diametrically across the cross section.

In certain embodiments, said portion consists of a plurality of rows of pixels, each row extending across the cross section, and the rows being parallel to one another.

In certain embodiments, said portion consists of a single row of pixels extending across the cross section, along a diameter of the cross section.

In certain embodiments, the apparatus further comprises a cylindrical pipe, arranged with its longitudinal axis vertical, arranged to contain a flowing sample, the sample volume being an interior volume of the pipe, and said cross section being a circular cross section of the pipe interior, in a horizontal plane.

In certain embodiments, the assumption of symmetry is that sample conductivity over said cross section is a function of radius only.

In certain embodiments, said perimeter is circular and said set of measurements comprises (or alternatively consists of) a first sub-set and a second sub-set, each of the first sub-set of measurements comprising driving a current between a respective pair of adjacent electrodes and measuring a voltage developed across a diametrically opposite pair of electrodes (i.e. the pair of current driving/exciting electrodes is diametrically opposite the pair of voltage measurement electrodes for each measurement of this first set), and each of the second sub-set of measurements comprises driving a current between a respective pair of adjacent electrodes and measuring a voltage developed across an opposite respective pair of electrodes along a respective chord of the circular perimeter (i.e. the pair of current driving electrodes and the pair of voltage measurement electrodes are generally at opposite ends of a respective chord of the circular perimeter for each of the second sub-set), wherein the chords of the second sub-set of measurements are parallel to one another.

In certain embodiments, the set of measurements consists of the first sub-set, the second sub-set, and a third sub-set, wherein the third subset comprises a plurality of measurements using respective pairs of electrodes at opposite ends of chords extending across the perimeter in a direction at least substantially perpendicular to the chords of the second sub-set.

In certain embodiments, the third sub-set further comprises a plurality of measurements using respective pairs of electrodes at opposite ends of further chords extending across the perimeter.

In certain embodiments, said further chords are short chords, each having a length no greater than the radius of the circular cross section.

In certain embodiments, each of the further chords extends in a direction neither parallel nor perpendicular to the chords of the second sub-set.

In certain embodiments, the plurality of electrodes consists of 16 electrodes, the first sub-set consists of 8 measurements, the second sub-set consists of 6 measurements, and the third sub-set consists of 6 measurements.

In certain embodiments, the processing means is adapted to calculate said sample conductivity values of said portion of the cross section from said set of measurements using a back-projection algorithm.

In certain embodiments, said set of measurements consists of no more than 50 measurements.

In certain embodiments, said set of measurements consists of no more than 20 measurements.

In certain embodiments, the apparatus further comprises a second plurality of electrodes arranged around a perimeter of a second cross section of the sample volume, each electrode of the second plurality being arranged to be in electrical contact with a sample contained in the sample volume, wherein the measurement means is adapted to perform a second set of measurements, each of the second set of measurements comprising driving a current between a first respective adjacent pair of said second plurality of electrodes and measuring a voltage developed across a second respective adjacent pair of said second plurality of electrodes, the processing means adapted to generate a second tomogram indicative of sample conductivity over said second cross section from said second set of measurements, and the processing means is further arranged to calculate sample conductivity values of a portion of said second cross section from said second set of measurements and generate said second tomogram from the calculated sample conductivity values of said portion of the second cross section using an assumption of symmetry.

A second aspect of the invention provided tomography apparatus comprising:

a plurality of electrodes arranged around a perimeter of a cross section of a sample volume for containing a liquid or mixed-phase sample, each electrode being arranged to be in electrical contact with a sample contained in the sample volume;

measurement means adapted to perform a set of measurements, each measurement comprising driving a current between a first respective adjacent pair of said electrodes and measuring a voltage developed across a second respective adjacent pair of said electrodes; and processing means adapted to generate a tomogram indicative of sample conductivity over a portion of said cross section from said set of measurements, characterised in that the set of measurements consists of no more than 50 measurements.

Features of embodiments of the first aspect, as described above, may be incorporated in embodiments of this second aspect, with corresponding advantage.

For example, in certain embodiments, said portion is one of: half of said cross section; a radial portion extending from a centre of the cross section to the perimeter; and a band extending diametrically across the cross section.

In certain embodiments, the plurality of electrodes consists of 16 electrodes, and the set of measurements consists of no more than 40 measurements. In certain embodiments, the set of measurements consists of no more than 20 measurements.

The arrangement of the electrodes and/or the set of measurements may be selected so as to provide relatively high resolution in the portion of sample cross section that is of interest. In applications where the flow of the sample in the conduit (e.g. through a bore of the conduit) has a degree of symmetry, the arrangement of electrodes and/or the set of measurements using the electrodes may be selected to image a portion of cross section that gives a good indication of a conductivity profile across the entire cross section. Thus, following principles disclosed in this specification, high resolution tomograms may be produced without needing as many measurements and/or electrodes as in prior art techniques.

Another aspect provides flow measurement or monitoring apparatus comprising tomography apparatus in accordance with any one of the above-described aspects and embodiments.

Another aspect (which again may incorporate one or more features as described above, with corresponding advantage) provides a tomography method comprising:

arranging a plurality of electrodes around a perimeter of a cross section of a sample volume for containing a liquid or mixed-phase sample, each electrode being arranged to be in electrical contact with a sample contained in the sample volume;

performing a set of measurements, each measurement comprising driving a current between a first respective adjacent pair of said electrodes and measuring a voltage developed across a second respective adjacent pair of said electrodes; and generating a tomogram indicative of sample conductivity over said cross section from said set of measurements, characterised in that the method further comprises calculating sample conductivity values of a portion of said cross section from said set of measurements and generating said tomogram from said calculated sample conductivity values of said portion using an assumption of symmetry.

Another aspect (which again may incorporate one or more features as described above, with corresponding advantage) provides a tomography method comprising:

arranging a plurality of electrodes around a perimeter of a cross section of a sample volume for containing a liquid or mixed-phase sample, each electrode being arranged to be in electrical contact with a sample contained in the sample volume;

performing a set of measurements, each measurement comprising driving a current between a first respective adjacent pair of said electrodes and measuring a voltage developed across a second respective adjacent pair of said electrodes; and generating a tomogram indicative of sample conductivity over a portion of said cross section from said set of measurements, wherein said set of measurements consists of no more than 50 measurements.

Another aspect provides a flow measurement method comprising use of a tomography method in accordance with any one of the above-described aspects and embodiments to generate a tomogram indicative of sample conductivity over at least a portion of a cross section of a flowing sample.

Further aspects and embodiments of the invention, and their associated features and advantages, will be apparent from the following description and the accompanying appendices.

BRIEF DESCRIPTION OF THE DRAWINGS

Embodiments of the invention will now be described with reference to the accompanying drawings, of which.

DETAILED DESCRIPTION OF THE PREFERRED EMBODIMENTS

Figure 1:
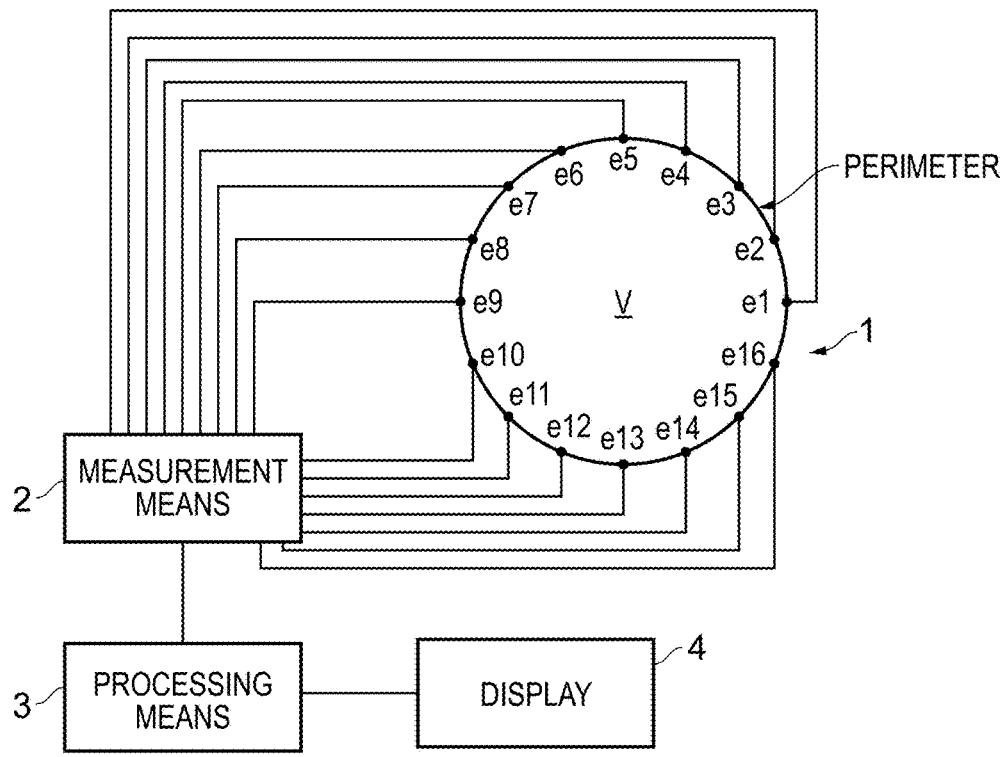
FIG. 1 is a schematic representation of tomography apparatus embodying the invention.

Referring now to FIG. 1, this shows tomography apparatus embodying the invention. The apparatus comprises an array of electrodes E1-E16 arranged around the perimeter of a sample-containing volume V. In this embodiment the perimeter is generally circular (for example the electrodes could be arranged around the circumference of a circular sample-containing vessel or conduit, such as a pipe) although in other embodiments the perimeter may have a different shape (for example electrical, square, rectangular, or any other shape). Also in this embodiment, the electrodes are equally spaced around the perimeter, but again, in alternative embodiments, the distribution of electrodes around the perimeter of the sample volume may not be uniform. The apparatus also comprises measurement means 2 (which may, for example, take the form of measurement apparatus, one or more measurement modules, or one or more measurement units). The measurement means is adapted to perform a set of measurements for imaging the conductivity of the sample cross section, each measurement comprising the use of one pair of adjacent electrodes to pass a current through the sample, and using a different pair of electrodes to measure a resultant voltage developed. In this embodiment, rather than making a set of 104 measurements with the 16 electrodes, the measurement means is adapted to make a reduced, smaller set of measurements. The reduced set of measurements is selected so as to enable the processing means 3 of the apparatus to calculate a tomogram having a resolution greater than, the same as, or comparable with the resolution of a tomogram producible from a set of 104 measurements over just a selected portion of the sample cross section. The apparatus further comprises display means 4 adapted to display a tomogram generated by the processing means (it will be appreciated that the processing means may, in certain embodiments, comprise a processor, or more than one processor).

In this embodiment, the "reduced" set of measurements made by the measurement means consists of 3 sub-sets. A first sub-set consists of 8 measurements, each measurement using a different selected 4 of the electrodes, and using a selected pair of adjacent electrodes to drive current through the sample and a diametrically opposite adjacent pair of electrodes on the cross section/perimeter to measure a resultant voltage. Thus, this first sub-set in certain embodiments may comprise a first measurement in which electrodes 1 and 2 are used to drive current and a voltage is measured between electrodes 9 and 10, a second measurement in which electrodes 3 and 4 are used to drive current and a voltage is measured across electrodes 11 and 12, a third measurement in which electrodes 4 and 5 are used to drive current and a voltage is measured across electrodes 12 and 13, etc, up to the eighth measurement in which electrodes 15 and 16 are used to drive current and the voltage is measured across electrodes 7 and 8. In alternative embodiments, this first set may comprise 8 measurements in which a first measurement consists of using electrodes 1 and 2 to drive current and electrodes 9 and 10 to measure voltage, a second measurement using electrodes 2 and 3 to drive current and electrodes 10 and 11 to measure voltage, etc, up to a final, eighth measurement in which electrodes 8 and 9 are used to drive current and electrodes 16 and 1 are used to measure a voltage. This first sub-set of measurements can thus be described as a set of rotary or diagonal measurements, with 8 projections. In this embodiment the second set of measurements consists of 6 measurements which can be generally described as parallel measurements with 6 projections, each measurement using two respective pairs of adjacent electrodes at opposite ends of a respective chord across the circular cross section, and the 6 chords being parallel to one another. In certain examples, this second sub-set consists of a first measurement using electrodes 2 and 3 to drive current and measuring a voltage between electrodes 15 and 16, a second measurement using electrodes 3 and 4 to drive current and measuring a voltage between electrodes 14 and 15, a third measurement using electrodes 4 and 5 to drive current and measuring a voltage between electrodes 13 and 14, a fourth measurement using electrodes 5 and 6 to drive current and measuring a voltage across electrodes 12 and 13, a fifth measurement using electrodes 6 and 7 to drive current and measuring a voltage between electrodes 11 and 12, and a sixth measurement using electrodes 7 and 8 to drive current and measuring a voltage between electrodes 10 and 11. In alternative embodiments, this set of 6 measurements can alternatively use the following pairs of electrodes to drive current in successive measurements; 2 and 3; 3 and 4; 4 and 5; 5 and 6; 6 and 7; and 7 and 8. In this first embodiment, the third sub-set of measurements consists of 6 measurements, the first using electrodes 1 and 2 to drive current and measuring a voltage between electrodes 8 and 9, the second using electrodes 9 and 10 to drive current and measuring a voltage between electrodes 16 and 1, the third using electrodes 10 and 11 to drive current and measuring a voltage between electrodes 8 and 9, a fourth using electrodes 7 and 8 to drive current and measuring a voltage between 9 and 10, a fifth using electrodes 15 and 16 to drive current and measuring a voltage between electrodes 1 and 2, and a sixth measurement using electrodes 2 and 3 to drive current and measuring a voltage between electrodes 1 and 16. In this third set, each measurement uses two pairs of electrodes at opposite ends of a respective chord of the circular perimeter. The set of chords includes two generally across, transverse, or perpendicular to those of the second set, and four relatively short chords, each having a length no greater that the radius of the cross section and being generally transverse to the two long chords used in this third set. Thus, in this first embodiment, and related embodiments, the set of measurements used to generate a tomogram of the sample cross section consists of just 20 measurements, that set consisting of a first set of generally diagonal or rotary measurements, a second set of generally parallel measurements across the sample volume, and a third sub-set consisting of 2 generally parallel measurements perpendicular to those of the second sub-set, and 4 generally transverse measurements at edges of the sample cross section. The processing means is adapted to generate a tomogram of a central band of the sample cross section from this reduced set of measurements, with the resolution of that tomogram in the band being comparable with that of a tomogram of the whole cross section produced using the prior art adjacent pair technique and a full set of 104 measurements. Thus, the apparatus is able to produce a high resolution tomogram in the region of interest more quickly, and with reduced processing, than prior art techniques.

Figure 2:
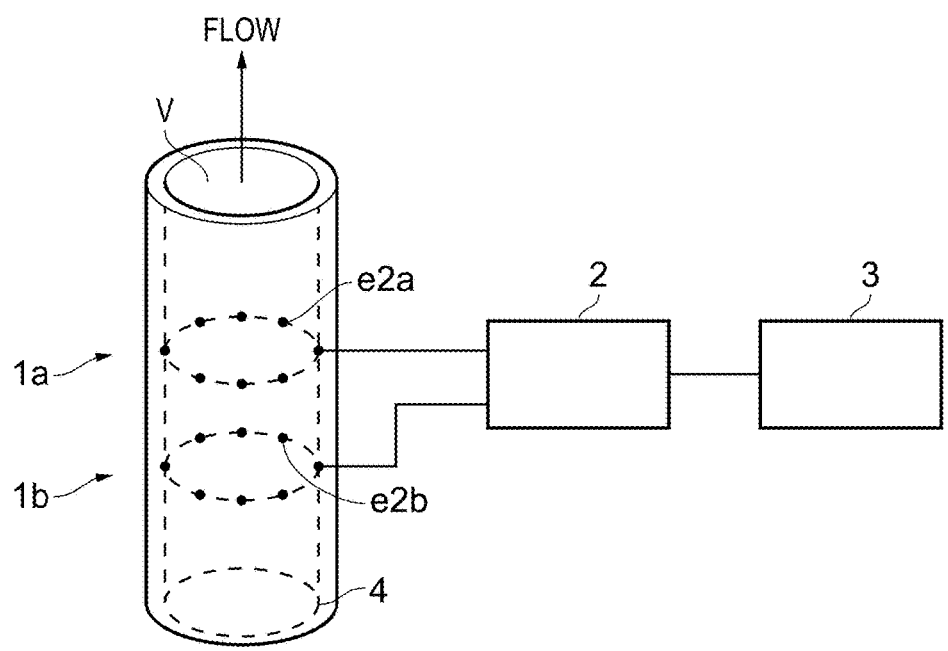
FIG. 2 is a schematic representation of flow measurement apparatus embodying the invention.

Referring now to FIG. 2, this shows flow measurement apparatus embodying the invention and including tomography apparatus also embodying the invention. This flow measurement apparatus comprises a conduit 4, which may also be described as a pipe, tube, or other generally cylindrical sample containing entity, the interior of which defines a sample containing volume V through which a sample may be arranged to flow. In this example, the sample is arranged to flow upwards in the direction generally indicated by the arrow, that is the longitudinal axis of the conduit 4 is arranged so as to be substantially vertical. This apparatus comprises first and second arrays 1a, 1b of electrodes, each of which is connected to the measurement means 2. The measurement means 2 is adapted to make respective sets of measurements using each of the first and second arrays of electrodes, and the processing means is adapted to calculate/generate tomograms indicating at least one parameter of the flowing sample as a function of cross section at the two different positions of the first and second electrode arrays. In other words, the electrodes of the first array 1a are arranged in a first plane generally perpendicular to sample flow, and the electrodes of the second array 1b are arranged at a second plane, generally parallel to the first plane. The apparatus is thus adapted to image at least one aspect of sample flow at each of the two planes. The measurement means is adapted to make a reduced set of measurements for tomogram generation, as compared with prior art techniques, and the processing means is thus able to generate tomograms indicative of sample cross sections at the two different planes more quickly than with prior art techniques.

Further aspects and advantages of embodiments of the invention will be appreciated from the following sub-sections of the description and associated commentaries.

Description Sub-Section 1

This sub-section is concerned with the effects of asymmetrical sensing and imaging on scalar and vector tomograms Summary The number and location of electrodes in a sensing array of an Electrical Impedance Tomography (EIT) application play an essential role in achieving the temporal and spatial requirements of specific process applications. Comparing the performance of an EIT with an 8-electrode array sensor, the one with 16-electrode array sensor provides more precise tomograms but the cost of slowing data acquisition speed. On the other hand, an important feature of developed multi-phase upwards pipeline flows is that the flow regimes can be assumed in radial symmetry over the cross-section of the pipe under the investigation, which means if a tomogram over a semiround or even along a radius of the cross section of the pipeline could be achieved, then the whole tomogram could be estimateable by mirroring and/or mapping them to the whole cross section. This section proposes an asymmetrical sensing and imaging (ASI) method and reports whether an 8-electrode sensing array in an asymmetrical distribution is feasible to reach an acceptable spatial resolution in both concentration and velocity measurements. A number of different electrode arrangements were investigated. The adjacent electrode sensing strategy was used for all asymmetrical arrangements. Experimental data was acquired from a gas-in-water upwards flow in a test pipeline with 5 cm inner diameter. Conductivity images were reconstructed with the sensitivity theorem based conjugate gradient method (SCG) and velocity distributions were calculated with a cross correlation method (AIMFlow). Results then were compared with those obtained with a conventional 16-electrode sensing array. Experiments were comprised of two steps. The first step was to investigate the most appropriate distribution of the 8 asymmetrical electrodes by evaluating the sensitivity maps and comparing the quality of images from pre-positioned cylindrical objects in a phantom. The second step was to investigate the performance, in terms of concentration and velocity profiles, of a chosen arrangement of the 8 asymmetrical electrodes for gas-water upwards pipeline flows, in comparison with the profiles sensed by conventional 16 electrodes. The results demonstrate that for static objects in the phantom, the proposed method produces better resolution than the conventional 8-electrode strategy, although it is still worse than the conventional 16 electrode sensing strategy. The advantages and limitations of the ASI method will be discussed.

Introduction

Conventionally, a number of electrode sensors (e.g., 8 and 16) are positioned equi-distantly around the process vessels, which provides continuous electrical contact with the electrolyte inside the process vessels. Given adjacent strategy and the number of electrodes N, the minimum number of independent measurement is determined by $N*(N-3)/2$ (Brown, 1987), which obviously indicates that the more the number of electrodes is, the more measurements it needs, resulting in longer time of data acquisition speed. However, in order to obtain better resolution of reconstructed images, it requires more electrodes to be applied. In our case, the data acquisition speed of V5R system (Jia, et al, 2010) with 8 electrodes is at 1250 dual-plane per second (dpfs), but the performance in terms of calculating concentration and velocity for each phase of multiphase flow is relatively poor. In contrast, the speed of V5R system with 16 electrodes is too slow (325 dpfs) to produce velocity profiles for multiphase flow. Therefore, there is a crucial demand to seek for an eligible solution of sensor design which reaches acceptable sensing speed while offers reasonable resolution of tomograms for multiphase flow metering without the expenses on hardware cost.

On the other hand, one significant characteristic of steady state upwards multiphase flow in vertical pipeline is that its cross-sectional tomograms can be estimated as symmetrical to the radius of the pipeline. In other words, if half of cross-sectional tomogram or even the area along the radius of the pipeline is measurable, the whole tomogram could be accomplishable by means of mirroring/mapping. According to this significant characteristic, an asymmetrically distributed 8-electrode array sensor could be used to replace the 16-electrode EIT system to produce cross-sectional semi-tomogram, in which case the sensing speed keeps the same as conventional 8-electrode EIT system, while the quality of the cross-sectional semi-tomogram could be better than the conventional 8-electrode system, even comparably similar to that of conventional 16-electrode EIT system.

This section is to investigate above feasibility of using an Asymmetrical Sensing and Imaging (ASI) method, in terms of concentration and velocity extraction for multiphase flows, with the constraints/assumptions that:

The multiphase flow under investigation is fully-developed gas-in-water 2-phase upwards flow in vertical pipeline;

SCG software (Wang, 2002) is applied to produce cross-sectional tomograms, due to that conventional sensitivity matrix is inapplicable to ASI-generated data;

AIMFlow is utilised to produce pixel concentration and velocity maps, but only the meaningful half is retained for further calculation;

Due to the limitation of available EIT systems, two different EIT systems are employed along the vertical pipeline to acquire the data by ASI and conventional 8- and 16-electrode strategy.

Experimental Settings

The primary goal of the experiments is to seek for an appropriate arrangement of asymmetrically-distributed 8 electrodes which has an improvement spatial resolution, in comparison with the conventional symmetrical arranged 8 electrodes system, for visualisation and measurement of vertical pipeline upwards multiphase flows. In order to achieve the goal, the experiments are set into 2 steps: the first is to determine the most eligible distribution of 8 asymmetrical electrodes which is capable of producing acceptable tomograms comparing to the ones produced by conventional EIT system with 8 and 16 electrodes; and the second step is to employ the selected ASI to gas-in-water vertical pipeline flow to evaluate the performance of the proposed ASI.

Determination of Eligible Distribution of ASI

Figure 3:
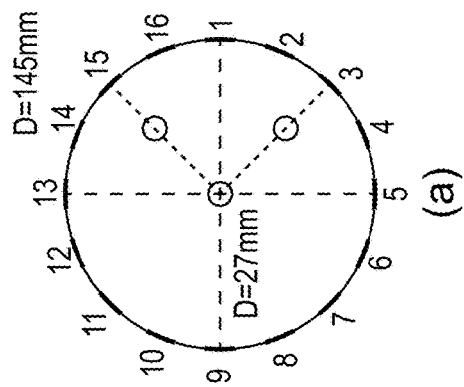
FIG. 3 illustrates physical positions of cylindrical objects in a small phantom. (a): x-axial mirror; (b): central quadric mirror; and (c): Pi-repetition.
Figure 3:
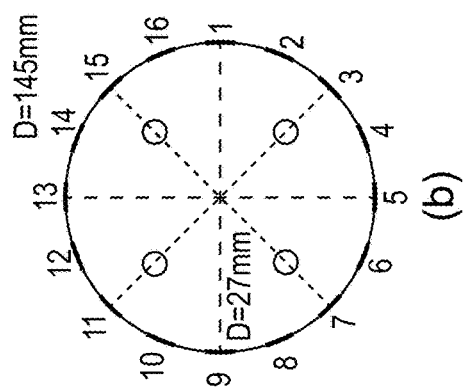
Figure 3:
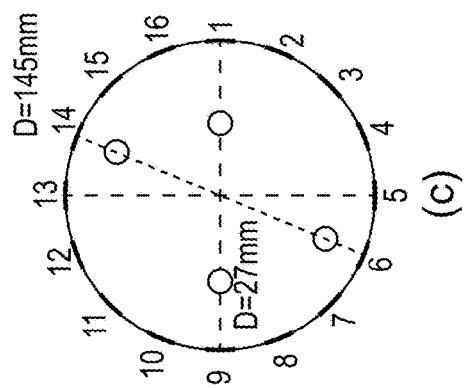
Figure 4:
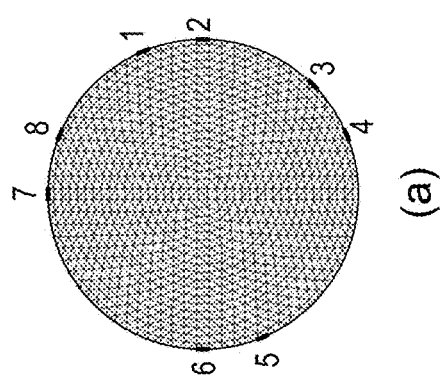
FIG. 4 illustrates mesh structures and electrode arrangements which may be used in embodiments of the invention, where (a): ASI-A; (b): ASI-B; (c): ASI-C.
Figure 4:
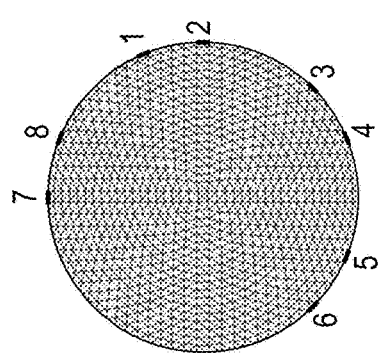
Figure 4:
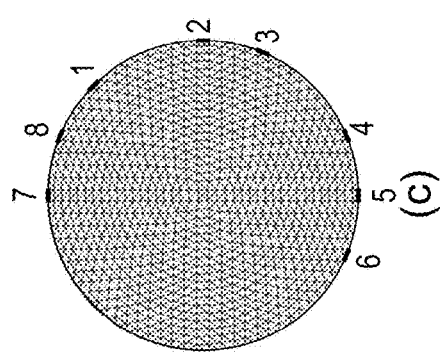

Overall, this step is to evaluate the performance of different distributions of ASI by means of comparing the tomograms of ASI to those produced by conventional 8 and 16 electrodes systems, and then select the most appropriate one for further experiments with various pipeline flows. All experiments in this step were conducted by means of positioning cylindrical objects (with diameter of 22 mm) in a small phantom (with diameter of 145 mm), depicted as FIG. 3, and then acquiring data with P2+ (ITS, 2009). For each different positioning of cylindrical objects in the phantom, 3 sets of data were acquired by 3 different sensing strategies, i.e., conventional 8 and 16 electrodes, and ASI with 3 different distributions. Finally, all data was processed by SCG software with the parameters of 841-node mesh structure, reconstruction steps=5, RMS=0.0001, and the number of inverse iterations=5. FIG. 4 depicts the applied mesh structures, and the electrode arrangements for the 3 different sensing strategies, which are utilised for determining the most appropriate ASI.

Evaluation of Selected ASI on Gas-in-Water Upwards Pipeline Flow

Figure 5:
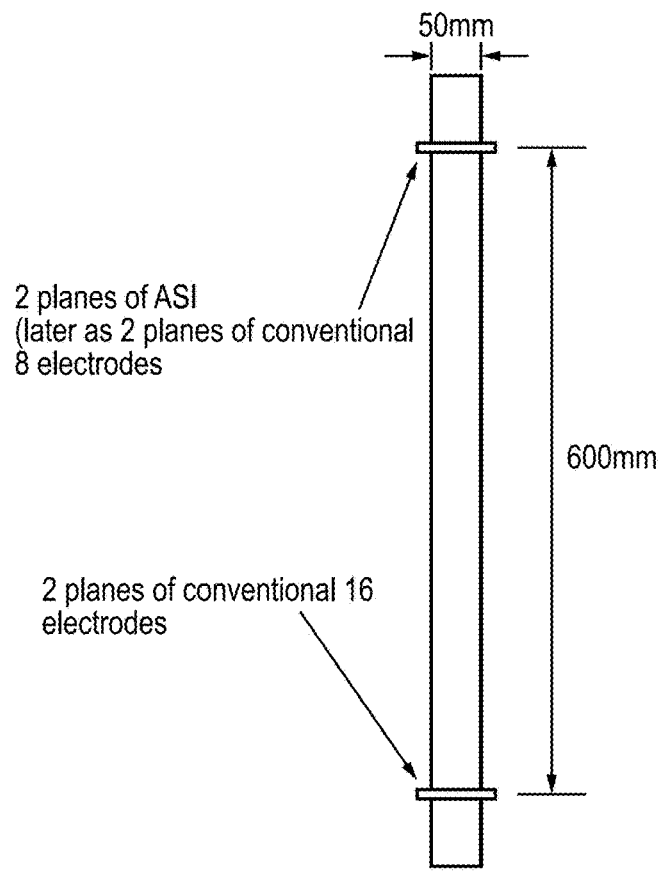
FIG. 5 illustrates the physical position of 2 sets of sensor arrays on a vertical pipeline in an embodiment of the invention.

In this step, two different flow regimes were tested, i.e., bubbly flow and slug flow, of which the water flow rate was fixed at 7.4 m3/h, and gas flow rate for bubbly flow and slug flow were fixed at 10 l/min and 70 l/min, respectively. For each flow regime, 3 sets of data were acquired: ASIs with V5R system, conventional 8 electrodes arrangement also with V5R system, and conventional 16 electrodes with FICA system (Wang, et al, 2005). The sensors were placed in the flow rig as shown in FIG. 5.

Figure 6:
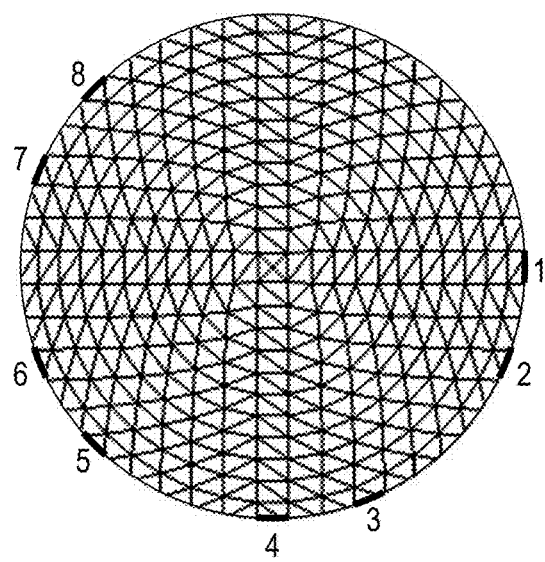
FIG. 6 illustrates a selected distribution of 8 asymmetrical electrodes based on mesh structure of 576 nodes in an embodiment.
Figure 7:
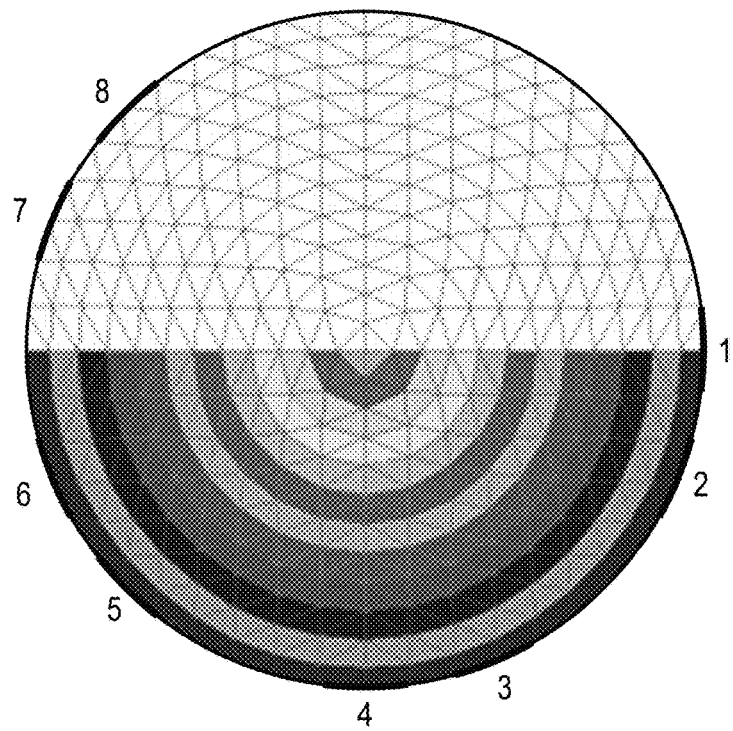
FIG. 7 illustrates two averaging strategies, showing elements used to generate profiles in an embodiment.
Figure 7:
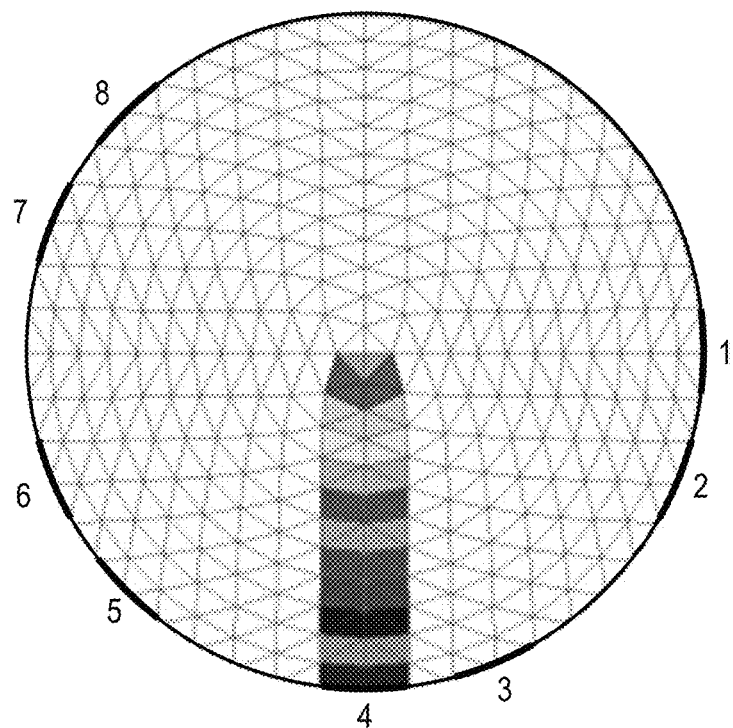

After the data being acquired, it was processed by SCG software (with 576 nodes) to generate reconstructed images. The mesh structure and sensor distribution of selected ASI, conventional 8 and 16 electrodes were shown as FIG. 6. Afterwards, the reconstructed images were handled by AIM-Flow software to produce concentration and velocity maps. Since not all the elements of the maps generated for selected ASI were useful, only the meaningful elements, as indicated in FIG. 7 and Table 1, were chosen for further processing. As depicted in FIG. 7, 2 different averaging strategies were applied for yielding profiles.

TABLE 1

Element indices used for averaging map to produce profile

| Profile element No. | Profile by bottom half | | Profile by bottom half of vertical central line | |
|---|---|---|---|---|
| | Mesh Indices | Total Number of Mesh | Mesh Indices | Total Number of Mesh |
| 1 (purple) | 1-46 | 46 | 22-25 | 4 |
| 2 (lavender) | 93-134 | 42 | 112-115 | 4 |
| 3 (indigo) | 177-214 | 38 | 194-197 | 4 |
| 4 (blue-grey) | 253-286 | 34 | 268-271 | 4 |

TABLE 1-continued

Element indices used for averaging map to produce profile

| Profile element No. | Profile by bottom half | | Profile by bottom half of vertical central line | |
|---|---|---|---|---|
| | Mesh Indices | Total Number of Mesh | Mesh Indices | Total Number of Mesh |
| 5 (turquoise) | 321-350 | 30 | 334-337 | 4 |
| 6 (light turquoise) | 381-406 | 26 | 392-395 | 4 |
| 7 (green) | 433-454 | 22 | 442-445 | 4 |
| 8 (lime) | 477-494 | 18 | 484-487 | 4 |
| 9 (yellow) | 513-526 | 14 | 518-511 | 4 |
| 10 (light yellow) | 541-550 | 10 | 544-547 | 4 |
| 11 (orange) | 561-566 | 6 | 562-565 | 4 |
| 12 (gold) | 573-576 | 4 | 573-574 | 2 |

Equation (1) explains the averaging strategies, where i is the index of target profile element, j is the indices of mesh defined in Table 1, N is the number of mesh involved in the different averaging strategies, and $Z_{i,j}$ is the value of concentration/velocity at mesh (i,j).

$$x_i = \frac{1}{N} \sum_{j=1}^{N} Z_{i,j} \quad (1)$$

$$i = [1, 12], \text{ and } j = [1, N]$$

Experimental Results

Figure 8:
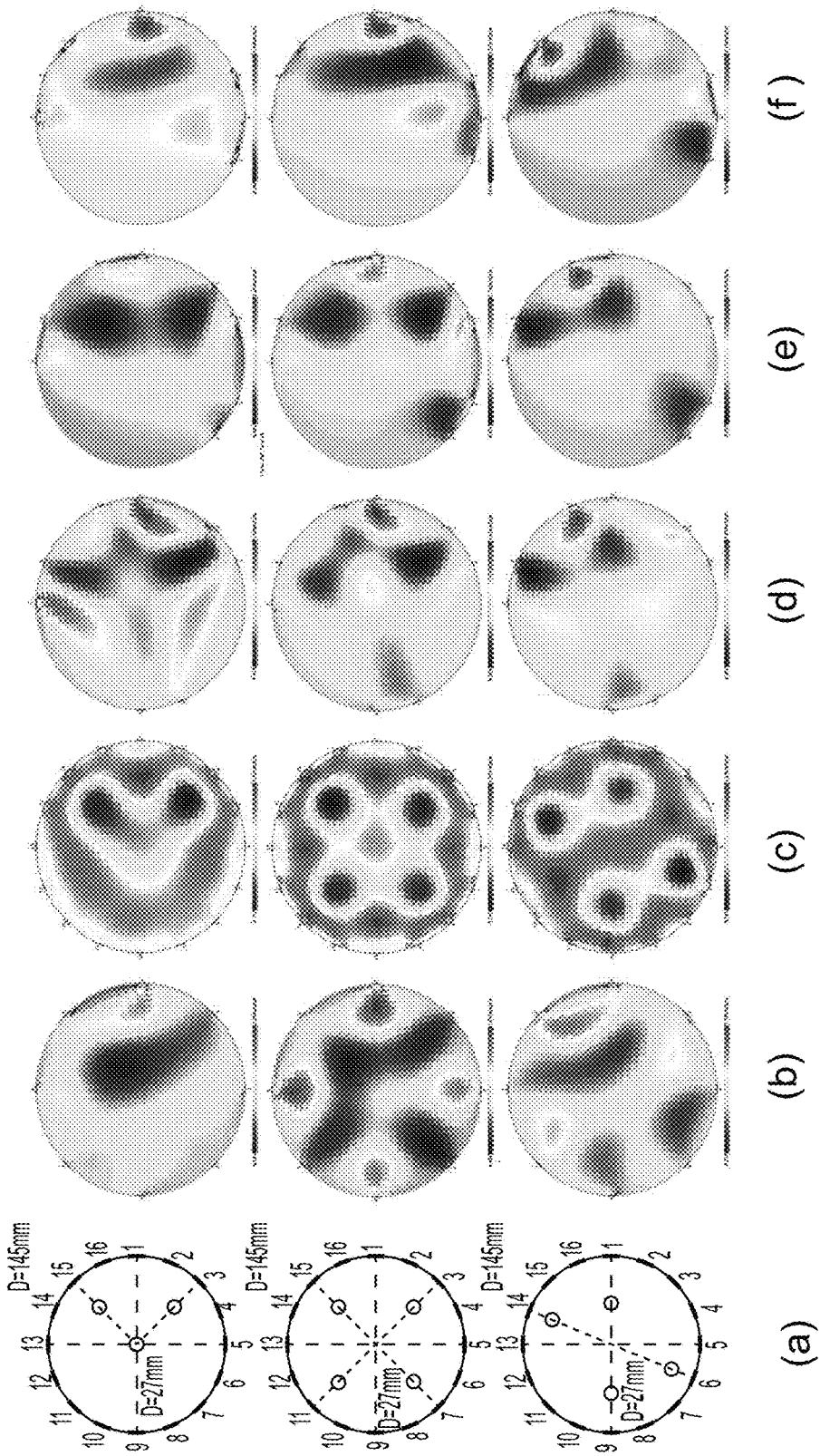
FIG. 8 shows SCG-generated tomograms of 3 different positioning of cylindrical objects in a small phantom by conventional 8 and 16 electrodes, and 3 different arrangements of ASI. (a): positionings of cylindrical objects in a small phantom; (b): tomograms by conventional 8 electrodes; (c): tomograms by conventional 16 electrodes; (d): tomograms by ASI-A; (e): tomograms by ASI-B; (f): tomograms by ASI-C.

FIG. 8 demonstrated the resulted tomograms from the first set of experiments. For each distribution of cylindrical objects, 5 tomograms were reconstructed with SCG with the same parameters, which were sensed by conventional 8 electrodes, conventional 16 electrodes, and the different ASIs (A, B, and C respectively). According to the arrangements of 8 electrodes in ASI, only the right half of the relating tomograms was concerned. The figure depicted that conventional 16 electrodes produced the highest resolution tomograms, while conventional 8 electrodes roughly identified the position of the static objects. Among the tomograms by 3 ASIs, the configuration B (the fourth tomograms for each distribution of cylindrical objects) outperformed the conventional 8 electrodes, while still worse than conventional 16 electrodes. Therefore, the ASI-B was chosen for further evaluation on gas-in-water vertical pipeline flow.

Figure 9:
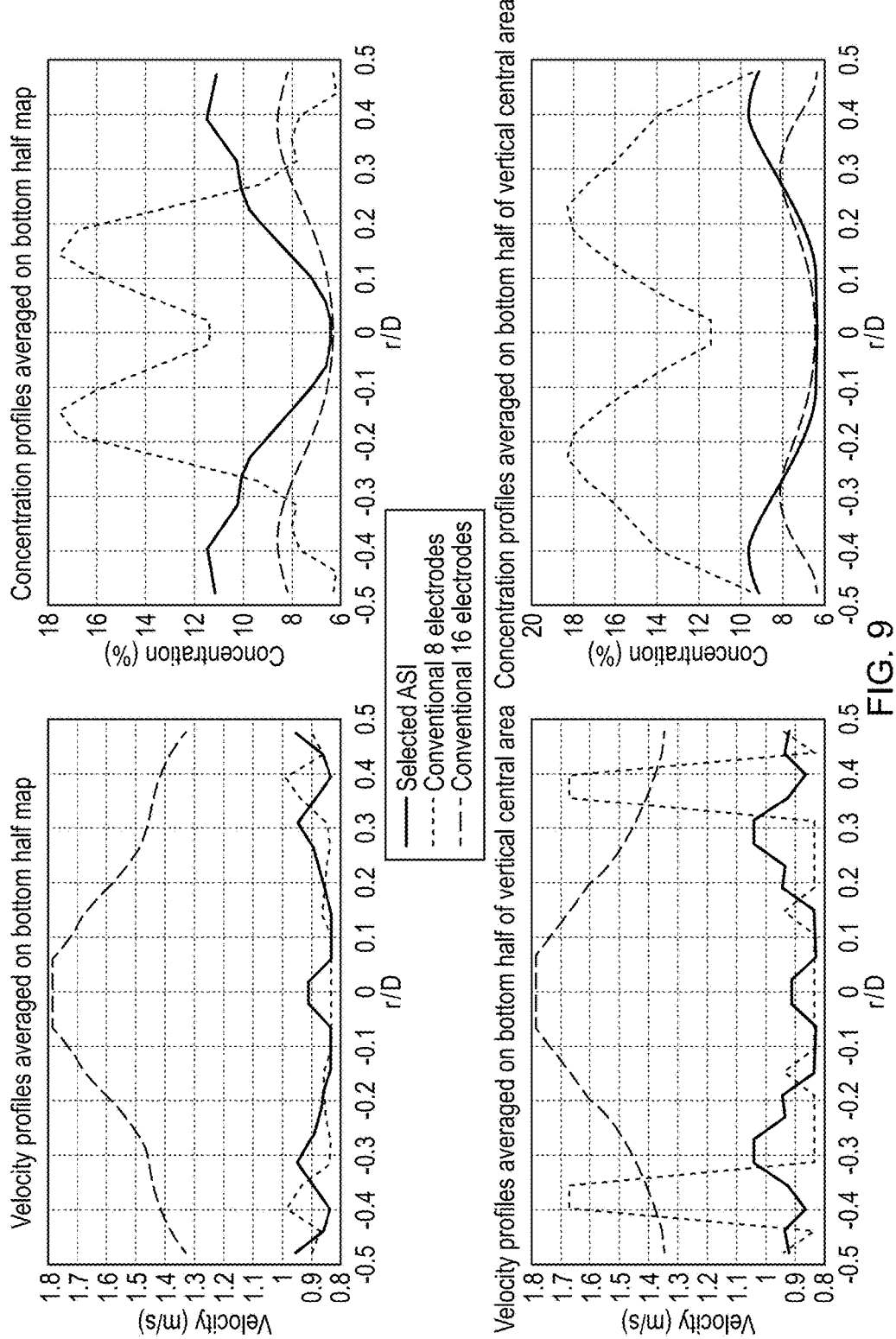
FIG. 9 shows concentration and velocity profiles of bubbly flow by selected ASI, conventional 8 electrodes and 16 electrodes.
Figure 10:
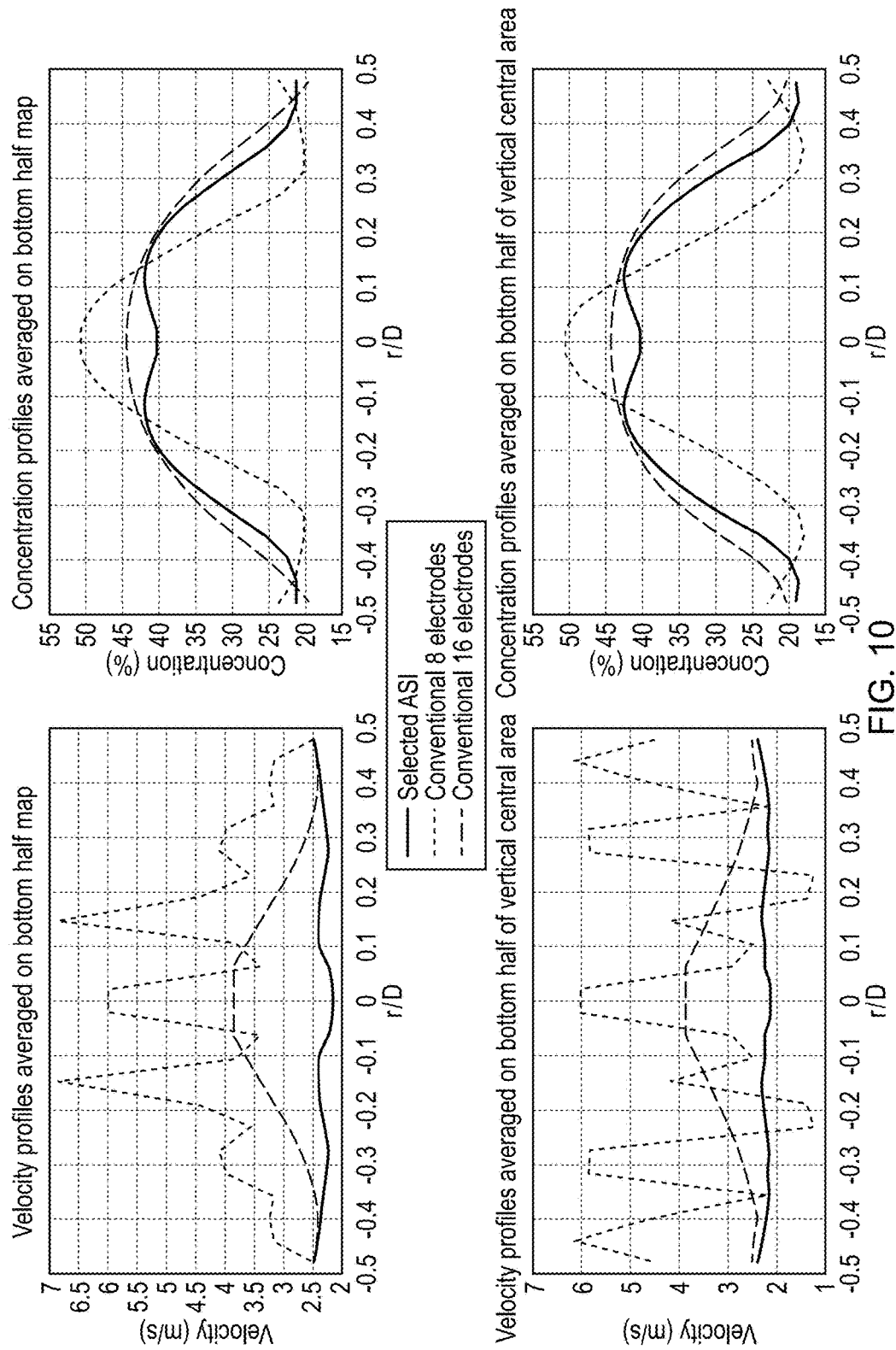
FIG. 10 shows concentration and velocity profiles of slug flow by selected ASI, conventional 8 electrodes and 16 electrodes.

Based on the selected ASI-B, the performance in regard to concentration and velocity profiles was evaluated on bubbly and slug upwards flows in vertical pipeline. FIG. 9 presents the profiles for bubbly flow, and FIG. 10 presents the profiles for slug flow, of which upper two charts were the profiles averaged on the bottom half of AIMFlow-generated maps, and bottom two charts were the profiles averaged on the bottom half of vertical central area of AIMFlow-generated maps. It can be concluded from FIG. 9 that although the ASI-generated velocity profile was similar to the profile by conventional 8 electrodes, both of which were worse than the one by conventional 16 electrodes, the ASI-generated concentration profiles were closer to the profiles by conventional 16 electrodes comparing to the one by conventional 8 electrodes. As far as slug flow was concerned, as depicted in FIG. 10, the performance of selected ASI was superior to that of conventional 8 electrodes, for both concentration and velocity profiles, although it was not better than conventional 16 electrodes.

In order to quantify the performance of ASI, relative errors were applied, defined as equation (2):

$$\text{Error}_{relative} = \left|\frac{x_{t,i} - x_{16e,i}}{x_{16e,i}}\right| \times 100\% \qquad (2)$$

$$i = [1, 12]$$

where t is either ASI or conventional 8 electrodes, $x_{t,i}$ is the value of either concentration or velocity at element i, and $x_{16e,i}$ is the value of either concentration or velocity at element i of by 16 electrodes. The results are presented in Table 2 and 3, in which the last row with bold numbers is the averaged relative errors of all 12 elements.

Table 2 shows that ASI and conventional 8 electrodes produced very similar results in regard to velocity profile of bubbly flow, and the averaged errors were even up to 43%. However, ASI outperformed conventional 8 electrodes in terms of concentration profile of bubbly flow. As far as slug flow was concerned, ASI produced better results with respect to both velocity and concentration than conventional 8 electrodes, and the improvement was significant, shown in Table 3.

TABLE 2

Relative errors for velocity and concentration profiles of bubbly flow by ASI and conventional 8 and 16 electrodes

| Velocity profile of bubbly flow | | | | Concentration profile of bubbly flow | | | |
|---|---|---|---|---|---|---|---|
| Averaged on bottom half | | Averaged on bottom half of vertical central area | | Averaged on bottom half | | Averaged on bottom half of vertical central area | |
| velocity profile by ASI | concentration profile by conventional 8 electrodes | velocity profile by ASI | concentration profile by conventional 8 electrodes | velocity profile by ASI | concentration profile by conventional 8 electrodes | velocity profile by ASI | concentration profile by conventional 8 electrodes |
| 27.91317602 | 32.29796642 | 31.06087665 | 30.16556167 | 36.47728966 | 23.05631121 | 42.4710781 | 47.35398684 |
| 37.78234203 | 37.01660117 | 30.65035193 | 38.3558766 | 33.77068003 | 26.50353817 | 45.03440784 | 77.33763059 |
| 40.93627997 | 30.19200535 | 36.73986379 | 20.76939046 | 33.25012565 | 10.49006957 | 33.37504084 | 94.38338929 |
| 38.16847008 | 35.06496351 | 34.30391203 | 18.30986065 | 26.3857956 | 6.404414892 | 17.77139962 | 92.78302573 |
| 34.81413337 | 41.81856776 | 27.61556423 | 42.09246528 | 22.98865749 | 5.762065835 | 6.989525889 | 97.62096426 |
| 39.25570555 | 43.83007863 | 29.72758514 | 43.7594189 | 26.8544654 | 18.02019421 | 0.478268519 | 115.9387032 |
| 43.02078539 | 44.4196673 | 38.92126205 | 45.84618404 | 28.94130557 | 77.57921466 | 3.823714891 | 136.3829374 |
| 46.46684918 | 46.54494791 | 41.52588531 | 48.33334677 | 25.8641094 | 133.3333204 | 6.233564326 | 145.5012604 |
| 50.1490685 | 48.46816483 | 49.66217007 | 43.75002625 | 18.69462462 | 155.7241522 | 6.256661406 | 140.6290696 |
| 51.66668793 | 51.66668793 | 51.66668793 | 51.66668793 | 9.895198138 | 143.1130259 | 4.302374143 | 129.6525402 |
| 53.33334453 | 53.33334453 | 53.33334453 | 53.33334453 | 2.428365099 | 109.0249658 | 1.637887743 | 106.4758373 |
| 48.88890382 | 53.33334453 | 48.88890382 | 53.33334453 | 0.380354606 | 78.43131117 | 0.380354606 | 78.43131117 |
| 42.69964553 | 43.16552832 | 39.50803396 | 40.80962563 | 22.16091427 | 65.62021534 | 14.06285649 | 105.2075547 |

TABLE 3

Relative errors for velocity and concentration profiles of slug flow by ASI and conventional 8 and 16 electrodes

| Velocity profile of slug flow | | | | Concentration profile of slug flow | | | |
|---|---|---|---|---|---|---|---|
| Averaged on bottom half | | Averaged on bottom half of vertical central area | | Averaged on bottom half | | Averaged on bottom half of vertical central area | |
| velocity profile by ASI | concentration profile by conventional 8 electrodes | velocity profile by ASI | concentration profile by conventional 8 electrodes | velocity profile by ASI | concentration profile by conventional 8 electrodes | velocity profile by ASI | concentration profile by conventional 8 electrodes |
| 1.32526278 | 0.38532085 | 5.07660701 | 78.71876503 | 9.24567927 | 21.94245656 | 1.12241 | 13.165416 |
| 0.44420996 | 30.53775381 | 7.36671932 | 146.3855608 | 5.76385228 | 4.039537195 | 12.758705 | 3.108158 |
| 1.5922231 | 34.19315478 | 8.72161733 | 85.80249461 | 12.2207202 | 18.79234547 | 19.337083 | 23.353966 |
| 5.81419113 | 27.99739258 | 13.30821 | 12.7451 | 13.4442869 | 31.67303497 | 18.426446 | 38.888698 |
| 12.5602506 | 54.95580263 | 17.1136176 | 121.4338236 | 10.1153664 | 39.12337922 | 13.412505 | 44.154297 |
| 18.3619422 | 50.44630006 | 22.1822262 | 109.5588092 | 5.10793999 | 35.9390087 | 7.908886 | 40.572083 |
| 21.1118076 | 22.27972005 | 25.5238051 | 58.35897108 | 1.57548593 | 24.5887557 | 3.774501 | 32.152017 |
| 25.1894533 | 40.34098678 | 28.2403286 | 56.02700213 | 0.41630252 | 12.25831202 | 1.512551 | 21.559337 |
| 29.6401089 | 100.4664257 | 32.1948287 | 22.80702517 | 1.23724152 | 1.83146626 | 1.063905 | 9.906509 |
| 33.396867 | 5.707058897 | 38.6009394 | 31.32076151 | 3.45101512 | 5.996458455 | 2.436022 | 1.492026 |
| 41.6902227 | 11.52777987 | 41.8901713 | 24.16666753 | 6.42760526 | 11.16593928 | 5.791699 | 10.207159 |
| 43.9655302 | 55.72916477 | 43.9655302 | 55.72916477 | 9.33875406 | 13.79524499 | 9.338754 | 13.795245 |
| 19.5910058 | 36.21390506 | 23.6820497 | 66.92117879 | 6.52868746 | 18.42882823 | 8.073622 | 21.029576 |

Discussion

A new sensor configuration based on asymmetrical distribution of 8 electrodes was investigated to calculate concentration and velocity of gas-in-water upwards pipeline flow, and our study demonstrated the performance of the proposed method. The new approach produced better resolution of tomograms, as well as concentration and velocity than the conventional 8 electrodes while the data acquisition speed retained as the same. Although the experiments were only on vertical pipeline, the approach is adaptable to horizontal and inclined pipeline flow by means of properly positioning 8 asymmetrical sensors, with the common assumption of developed multiphase flows in horizontal and inclined pipeline to be symmetrical to the vertical diameter of pipeline.

However, there are still few aspects need further investigation. First of all, more ASI configurations should be examined to find the most appropriate one by means of simulating sensitivity field and then experimenting different positioning of static objects. In addition, there should be a more appropriate averaging strategy which deserves further exploration since two different strategies produced different relative errors. Besides, improving signal-to-noise ratio would be definitely suitable for reducing noise and therefore increasing experimental precision. Another aspect is to investigate the feasibility of proposed method to horizontal and inclined pipeline flow by carefully designing sensor distribution.

REFERENCES

BROWN, B. H., AND SEAGAR, A. D., (1987), The Sheffield data collection system. Clinical Physics and Physiological Measurement, 8(4A):91.

ITS (2009), P2+ Electrical Resistance Tomography System—User's Manual, Speakers House, 39 Deansgate, Manchester M3 2BA JIA, J. B., WANG, M., SCHLABERG H. I., AND LI, H., (2010) A novel tomographic sensing system for high electrically conductive multiphase flow measurement, Flow Measurement and Instrumentation, vol. 21, no. 3, pp. 184-190.

WANG, M., (2001), Inverse Solutions for Electrical Impedance Tomography Based on Conjugate Gradients Methods, Measurement Science and Technology, 13, 101, pp. 101

WANG, M., MA, Y. X., HOLLIDAY, N., DAI, Y. F., WILLIAMS, R. A., LUCAS, G., (2005) A high-performance EIT system, Sensors Journal, IEEE, vol. 5, no. 2, pp. 289-299.

Comments on Sub-Section 1

Referring now to sub-section 1 above, that sub-section discloses further embodiments of the present invention and further background information useful for understanding the invention. As will be appreciated from the introduction, certain embodiments of the invention use the assumption that when the sample-containing volume is the interior volume of a vertical pipe or conduit with a circular cross section, if the flow is upwards and at steady state then the properties of the flowing sample can be assumed to be symmetrical to the radius of the pipeline. In other words, sample parameters/flow conditions can be assumed to be a function of radius only. Thus, in certain embodiments of the invention a limited set of measurements using the array of electrodes is made and the processing means can initially calculate a tomogram of just a portion of the sample cross section, that partial tomogram extending from the centre of the cross section in a radial direction to an edge of the cross section. Satisfactory resolution can be achieved for this portion of the cross section using a reduced set of measurements (and hence at high speed), and then the apparatus may be adapted to use the assumed symmetry of sample properties/flow properties to construct a tomogram of the full cross section. Thus, a reduced set of measurements is used to calculate tomogram data for a portion of the sample cross section, and then a full tomogram is calculated/constructed, using symmetry assumptions, from that "partial tomogram", rather than directly from the reduced set of measurement results.

It will also be appreciated from the introduction of sub-section 1 that in embodiments where the sample-containing volume is the interior volume of a horizontal pipe or conduit having a circular cross section (or other cross section symmetrical about a vertical axis) then a valid assumption for steady-state flow is that sample properties/parameters and/or flow conditions are symmetrical in the conduit about the vertical axis. Thus, for flow in a horizontal pipe, tube, or other conduit, a reduced set of tomography measurements can be used to calculate a high resolution tomogram of one vertical half of the sample/flow cross section, and a full tomogram can be constructed by simply mirroring this calculated half. A reduced set of measurements can therefore be used on a horizontally flowing sample and yet achieve a high resolution image of the entire cross section with reduced processing as compared with prior art techniques.

FIG. 4 shows three different asymmetric arrays of electrodes in different embodiments of the invention. Each of these arrays consists of 8 electrodes arranged asymmetrically around the circumference or perimeter of a sample cross section or sample-containing volume, in contrast to prior art arrangements in which 8 electrodes were typically arranged evenly around the perimeter. In each of these embodiments the processing means was arranged to perform a set of measurements, each measurement using an adjacent pair of electrodes to drive current through the sample and a different pair of adjacent electrodes to measure a resultant voltage.

As will be appreciated from sub-section 1 above, in certain embodiments of the invention an asymmetric array of electrodes is used to perform a set of measurements, and processing means is then adapted to calculate a tomogram of the entire cross section of the sample. Then, half of that tomogram is discarded (i.e. in embodiments where the array of electrodes and associated measurements are adapted to provide relatively high resolution for just one half of the sample cross section), and then a final tomogram of the entire cross section can be constructed by mirroring the un-discarded half of the original tomogram. This technique is applicable for both vertical flow and horizontal flow, where the electrode arrangement and associated measurement strategy is adapted to provide higher resolution in one vertical half of a sample cross section in the case of horizontal flow. In other embodiments, suitable for imaging vertical flows, an initial tomogram is constructed of the entire sample cross section and then all but a radial band of that initial tomogram, corresponding to a region of the cross section for which the electrode arrangement and set of measurements provides highest resolution, are discarded. A final tomogram can then be constructed from the retained band, such that the final tomogram also has the resolution of that selected band.

In FIG. 7 and Table 1 of sub-section 1, the profile element No 1 described as being purple corresponds to the outer ring in FIG. 7, and profile element No 12 (gold) is the inner ring (i.e. at the centre of the cross section).

Description Sub-Section 2

This sub-section is concerned with a method of partial Imaging with Limited Measurements.

Summary

A new sensing strategy through specially arranged excitation and measurement positions has been invented, which only uses 20 measurements but provides a similar spatial resolution at part of imaging area as that of the adjacent electrode pair sensing strategy with 104 independent measurements, so called Partial Imaging with Limited Measurements (PILM). Therefore, it is expected the data capture speed can be greatly enhanced without reducing the imaging spatial resolution with PILM.

Description

PILM Sensing Strategy

It is a basic and necessary requirement to have sufficient data capture rate to approach the required accuracy of velocity measurement in the use the cross correlation method (CC). It is known the discrimination error is expressed to assess the accuracy in the use of EIT.

$$\kappa = \delta/2\tau \qquad (1)$$

where $\tau$ is the time required for a flow passing the due-plane sensor.

If the distance between the two sensing planes of a dual-plane sensor is 0.05 m and flow velocity is 10 ms$^{-1}$ then $\tau = 0.05$ m/10 ms$^{-1}$ = 0.05 s. For a discriminatory precision of 0.05 or 5%, $\delta = 0.0005$ s, the speed of 2000 dual-frames per second (dfps) required. To distinguish the slip velocity between oil and gas, for example, a high accuracy at 1% or better discrimination error is expected, which is corresponding to a data capture rate about 10,000 dfps. It is obviously challengeable to the current system. An alternative way to enhance the data rate of existing system is to reduce the number of electrodes per sensor, e.g. from 16 to 8. However, the spatial resolution from 8-electrode sensor is dramatically reduced, which cannot satisfy the requirement for imaging flow regime.

The new method is based on a 16-electrode sensor, in which electrodes are arranged equal distance around internal wall of the vessel or pipe. A new sensing strategy through specially arranged excitation and measurement positions is invented, which can remain a similar spatial resolution as the performance of 16-electrode sensor at part of imaging area, but with very limited measurements, so called Partial Imaging with Limited Measurements (PILM). Therefore, it is expected the data capture speed can be greatly enhanced.

As a specific example of a developed pipeline multiphase flow measurement, the flow characteristics, e.g. the disperse phase concentration and velocity distributions can be assumed as either radial symmetrical (the pipeline in vertical layout) or central-vertical plane symmetrical (the pipeline in horizontal layout). To combine bother cases, the necessary and minimum imaging area, which can represent the major features of pipeline flows, is the row of pixels along the central-vertical plane, as indicated below.

Figure 12:
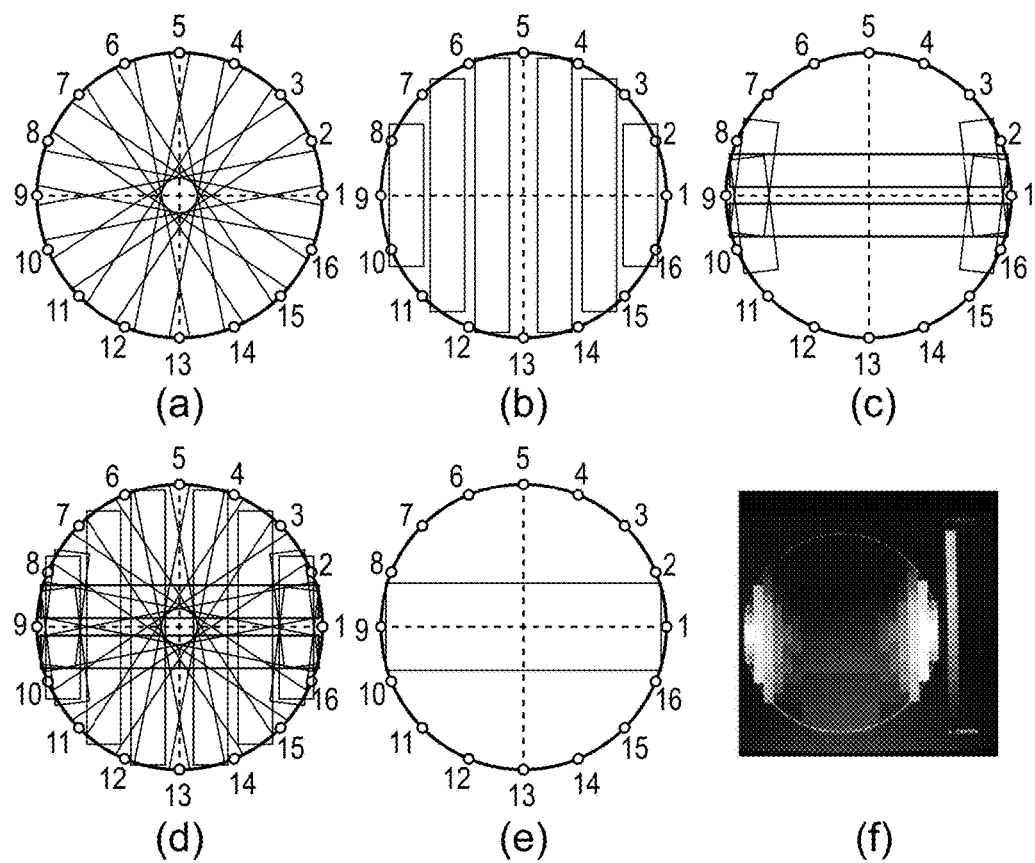
FIG. 12 illustrates a PILM sensing strategy used in certain embodiments, (a) Rotary with 8 projections, (b) Parallel with 6 projections and (c) Complimentary with 6 projections, (d) Overall projections, (e) High sensitive region, (f) actual sensitivity distribution.

The new sensing strategy consists of three groups of excitations and measurements as the rotary, parallel and complimentary projections given in FIG. 12, which relates to 8, 6 and 6 of a total 20 projections, respectively. Each projection is carried out by applying current to a pair of electrodes and measuring voltage from other pair of electrodes as illustrated electrode pairs adjacent to the two terminals of each rectangular bar in FIG. 12. Based on the reciprocity theorem, no mutual projection (excitation and measurement) is required. The overall projections and the expected high sensitive region are shown in FIGS. 12(d) and (e) respectively.

PILM Imaging Reconstruction

Figure 13:
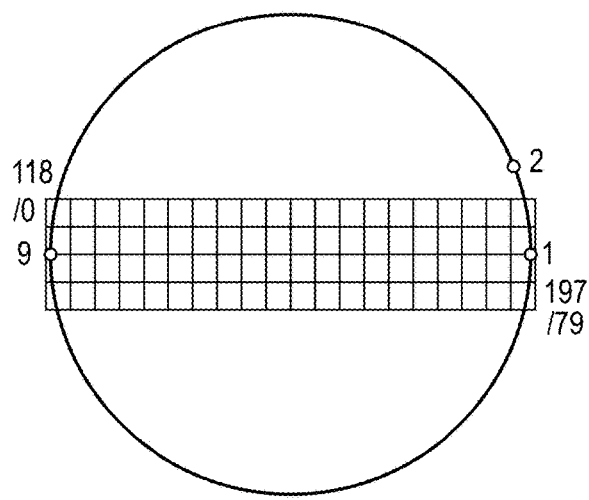
FIG. 13 illustrates the pixels used in one partial imaging technique embodying the invention.

In consideration of online flow measurement, the sensitivity back-project algorithm (SBP in Equation 1) is used for rapid imaging. Only very limited pixels are involved in the PILM imaging. For example of given pixels in domain of interests in FIG. 13, a sensitivity distributions from the 20 projections on the total of 80 pixels is calculated, which gives 1600 sensitivity coefficients.

$$\left[\frac{\Delta \sigma^n}{\sigma_0}\right]_N^V \propto [S_{n,m}]_{N,M} \times \left[\frac{\Delta V_{meas}^m}{V_{ref}^m}\right]_M^V \qquad (1)$$

where, S is the sensitivity matrix, N=80, M=20, n=1, 2, . . . N and m=1, 2, . . . M.

Initial Test Results

Figure 14:
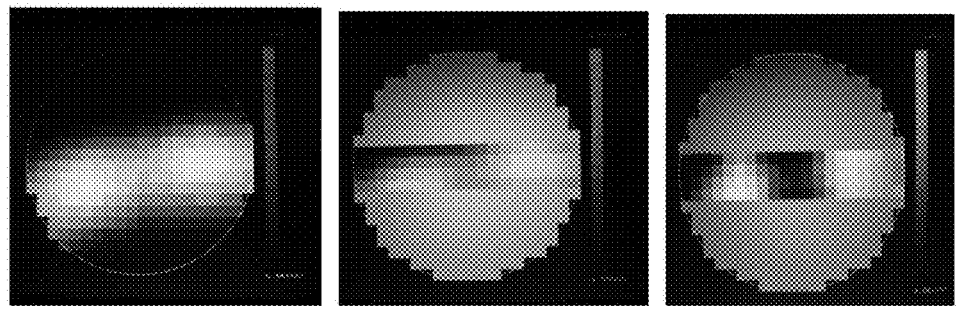
FIG. 14 shows imaging results in an embodiment of the invention.

Illustrations of the performance are given in FIG. 14 for a simulated set-up with two low conductive objects. FIG. 14(a) is the two objects sensed by the adjacent electrode pair method and reconstructed with SBP and FIG. 14(b) is part of the image (a). FIG. 14(c) is the two objects sensed by PILM and reconstructed with SBP.

Comments on Sub-Section 2

Referring now to subsection 2 above, this describes further embodiments of the invention and further background information useful for understanding the invention. FIG. 12 illustrates a reduced set of measurements in certain tomography apparatus and methods embodying the invention. The reduced set of measurements is selected so as to enable the processing means to produce a high-resolution tomogram over a central (i.e. generally diagonal) band across the sample cross section, and that high resolution band can be used with suitable assumptions of symmetry, as discussed elsewhere in the specification, to construct a tomogram of the entire cross section at the same resolution as the band. As can be seen from FIG. 12, the set of measurements consists of a first sub-set of rotary/diagonal measurements, a second sub-set of "parallel" measurements, and a third sub-set of measurements. In the first sub-set, just half of the array of 16 electrodes can be used for driving current (e.g. where the measurements use electrodes 1 and 2, then 2 and 3, then 3 and 4 etc. for driving current) or all of the electrodes can be used for driving current (in which case a first measurement would use electrodes 1 and 2, a second measurement would use electrodes 3 and 4, a third measurement would use electrodes 5 and 6, etc. for driving current). In each measurement, the voltage is measured at the respective diametrically opposite pair of electrodes from the driving pair. In the second sub-set, all of the current driving electrodes may be selected from one half of the array cross section (e.g. using electrodes 2 and 3, then 3 and 4, then 4 and 5, then 5 and 6, then 6 and 7, then 7 and 8 to drive current), or in alternative embodiments the position of the driving pair of electrodes can alternate from one side of the array to the other (for example the first measurement may use electrodes 2 and 3 to drive current, then the second measurement may use electrodes 14 and 15 to drive current, the third measurement may use electrodes 4 and 5 to drive current etc.). In each case, the voltage measured is that developed across a pair of electrodes opposite the driving pair, in a direction generally parallel to the line extending between electrodes 5 and 13. The third sub-set of measurements includes two measurements generally transverse to the "parallel" measurements of the second sub-set, and then 4 measurements generally at the edges of the sample cross section. FIG. 12d shows the full set of 20 measurements used in this embodiment, and FIG. 12e shows the central band or portion of the sample cross section at which the reduced set of 20 measurements yields highest accuracy and resolution. This region may comprise 80 pixels, in 4 rows of 20. Suitable methods for deriving sample conductivities for each of these 80 pixels from the set of 20 measurements described in sub-section 2 will be apparent to the skilled person from the prior art, the contents of this specification, and from the references cited in this specification, the contents of each of which are incorporated herein by reference.

In general, in the use of the simple back projection algorithm, the matrix multiplication is made by M×N=m, where M is the number of pixels, N is the number of boundary measurements, and m is the resultant pixel conductivities. Using the PILM technique described in this specification, N is down from 104 (for the conventional adjacent-electrode scheme applied to an array of 16 electrodes) to 20, M is down from 316 to 80 with the same pixel resolution, and m is the same number of pixels in the domain as M. N=20 is beneficial to the hardware construction and data acquisition speed. In the examples described in sub-section 2, M is 80, but in certain alternative embodiments M could be reduced even just to 20 along the diameter without loss of resolution. In other words, in certain embodiments, a reduced set of measurements can be used to calculate sample conductivities for each of just a single row of pixels extending along a diameter of the sample cross section. This calculated row of pixels can then be used, assuming sample parameters and flow properties are a function of just radius in the case of vertical flow, to construct a relatively high resolution tomogram of the entire sample cross section.

Description Sub-Section 3

This sub-section is also concerned with methods of partial imaging with limited measurements.

Background

It is a basic and necessary requirement to have sufficient data capture rate for a cross correlation method. It is known the discrimination error is expressed as CC method to extract the velocity distribution in the use of EIT.

$$\kappa = \delta/2\tau \quad (1)$$

where $\tau$ is the time required for a flow passing the due-plane sensor. If the distance between the two sensing planes of a dual-plane sensor is 0.1 m and flow velocity is 10 ms$^{-1}$ then $\tau=0.1$ m/10 ms$^{-1}$=0.01 s. For a discriminatory precision of 0.05 or 5%, d=0.001 s, the speed of 1000 frames/s is required.

The available EIT system, e.g. the FICA system developed by the University of Leeds, can capture 1000 dual-frame per second (dfps), but it was not designed for handling high conductive fluids, such as seawater. The voltage drive system also developed by Leeds have an excellent performance to manage high conductive fluids with a reasonable data capture speed, typically, 300 dfps in the use of 16-electrode dual-plane sensor and more than 1000 dfps in the use of 8-electrode dual-plane sensor. Recent investigation indicated that mean values of flow quantities can be achieved in the use of 8-electrode sensor, but not the flow pattern. It may create further challenge for flow regime recognition due to its very limited spatial resolution. The options seems only two by either further developing a fast system with feature of handling high conductive fluids as that of the voltage drive system, or remaining the status of current new VMMF without good capability for visualisation in the use of 8-electrode sensor.

The concept of asymmetrical sensing imaging (ASI) has been considered by the present inventors. The initial idea was to use very limited number of electrodes and generate a sensing map only having high imaging sensitivity at part of the traditional disk-shape imaging area. In principle, it should work but after various tests conducted at Leeds, the results did not demonstrate its high advantage although the resolution at partial area can be enhanced and better than that obtained with a classical 8-electrode sensor. Unfortunately, it is still much below the acceptable resolution.

The new approach is based on a 16-electrode sensor, which has the same configuration as the classical sensor. By a careful selection of existing excitation and projection position, to remain a similar performance of 16-electrode sensor at part of imaging area, but with very limited measurements, so called Partial Imaging with Limited Measurements (PILM). Therefore, it is expected the data capture speed can be greatly enhanced.

Principles

In our previous discussion, it was understood the relative change of conductivity is a function the relative change of boundary voltage, which present a pure linear relationship $$\left[\frac{\sigma_x^n(T_x)}{\sigma_1(T_x)}\right]_N^V \propto [S_{n,m}]_{N,M} \times \left[\frac{V_{meas}^m(T_x)}{V_{ref}^m(T_x)}\right]_M^V \quad (2)$$

Setting Zero Value Based on a Transformation Matrix

Therefore, the manipulation of the matrix production with a specific set of boundary excitations/measurements becomes a simple operation, which is illustrated as below.

$$[R]_N^V \propto [A]_{N,M'}[X]_{M'}^V$$

Assuming a number of terms in [X] is zero with a known rank. Then, a transforming matrix can be built, in which its diagonal terms follows up the specific value in either 1 or 0 in the rank illustrated as below, $$[T]_{M,M} = \begin{bmatrix} 0 & 0 & 0 & 0 & 0 \\ 0 & 1 & 0 & 0 & 0 \\ 0 & 0 & \cdot & 0 & 0 \\ 0 & 0 & 0 & \cdot & 0 \\ 0 & 0 & 0 & 0 & \cdot \end{bmatrix}_{M,M}$$

The specified vector [X'] can be expressed as, $$[X']_{M'}^V = [T]_{M,M'}[X]_{M'}^V$$

where some terms in [X] is signed as zero after the transformation.

$$[R]_N^V \propto [A]_{N,M'}[T]_{M,M'}[X]_{M'}^V$$

Based on the role of the matrix multiplication, the order of the processes can be made in both ways, as indicated in below $$[R]_N^V \propto \{[A]_{N,M'}[T]_{M,M'}\} \cdot [X]_{M'}^V \text{ or } [R]_N^V \propto [A]_{N,M'} \{[T]_{M,M'}[X]_{M'}^V\}$$

The Central Rows of Pixels in Pipeline Flows

Figure 11:
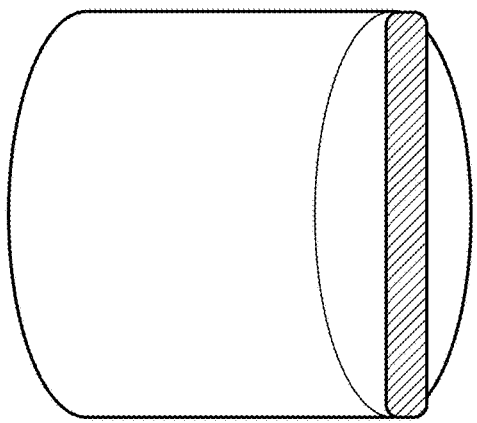
FIG. 11 illustrates a symmetrical feature in developed pipeline flows.

Form developed pipeline multiphase flows, the flow characteristics, e.g. the disperse phase concentration and velocity distributions can be assumed as either axial symmetrical (pipeline in vertical layout) or central-vertical plane symmetrical. To combine both cases, the necessary and minimum imaging area, which can represent the major features of pipeline flows, is the row of pixels along the central-vertical plane, as indicated in FIG. 11.

Figure 15:
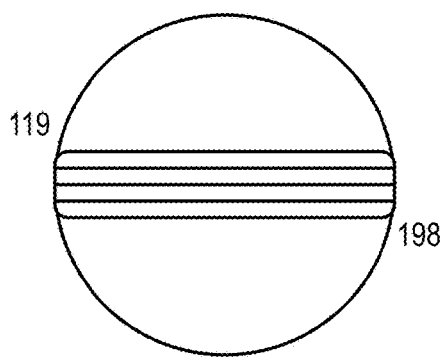
FIG. 15 illustrates a set of pixels used for imaging in an embodiment of the invention.

Back to the square mesh/pixels used in the image reconstruction, the specific imaging area along the central-vertical rows gives the most convenient process, which has a continuous order in the current square mesh definition. For example, for the mesh with 316 pixels and 4 rows of 20 pixels along either x- or y-axis it starts from 119 and ends at 198 (see FIG. 15).

$$[R']_N^V \propto [A']_{119-198,M'} \cdot [[X']_{M'}^V]$$

where [A] has zero value for terms from 1 to 118 and from 199 to 316. The matrix can be further reduced in the consideration of zero value in [X']

$$[A']_{N,M} = \begin{bmatrix} 0 & 0 & 0 & 0 & 0 \\ x & x & x & x & x \\ x & x & x & x & x \\ x & x & x & x & x \\ 0 & 0 & 0 & 0 & 0 \end{bmatrix}_{119-198,M} \Rightarrow \begin{bmatrix} 0 & 0 & 0 & 0 \\ 0 & x & 0 & x & 0 \\ 0 & x & 0 & x & 0 \\ 0 & x & 0 & x & 0 \\ 0 & 0 & 0 & 0 \end{bmatrix}_{119-198,M}$$

$$\cdot [X']_M^V = \begin{bmatrix} 0 \\ y \\ 0 \\ y \\ 0 \end{bmatrix}_M \begin{bmatrix} y \\ y \end{bmatrix}_M \Rightarrow$$

$$[R']_{N'} = \begin{bmatrix} x & x \\ x & x \\ x & x \end{bmatrix}_{119-198,M} \times \begin{bmatrix} y \\ y \end{bmatrix}$$

Imaging the Central Rows of Pixels

It consists of three sets of projections: rotary with 8 measurements; 6 parallel measurements, and 6 complimentary measurements, as shown in FIG. 12, together with the overall set of measurements and the expected sensing band.

Figure 16:
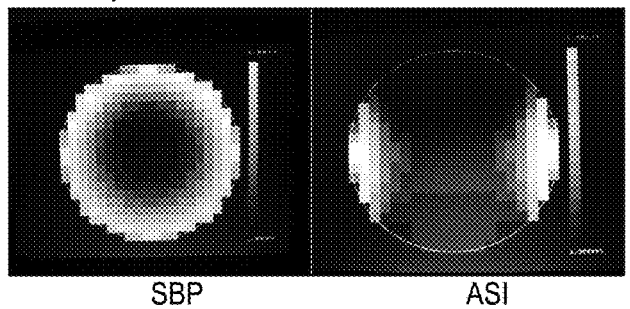
FIG. 16 illustrates test results in an embodiment of the invention.
Figure 16:
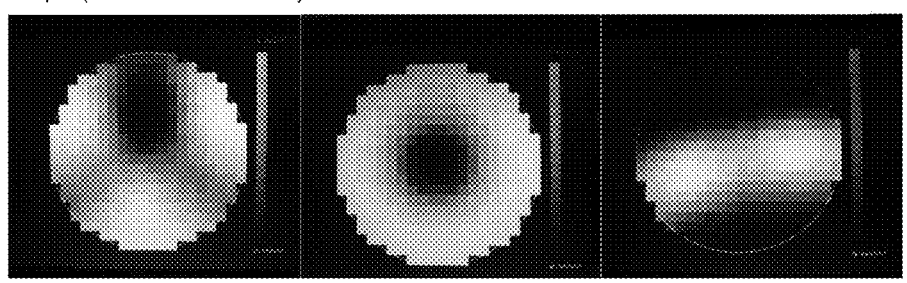
Figure 16:
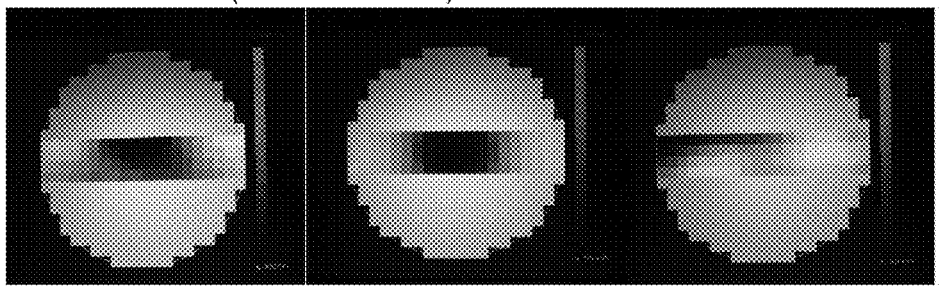
Figure 16:
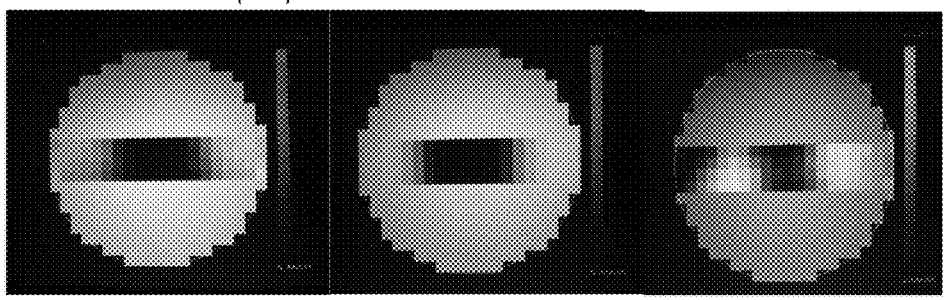

Initial test results are shown in FIG. 16

Conclusion

The proposed ASI method for imaging the central band shows an excellent resolution approaching the conventional SBP, but only 20 measurements are used. It shows the potential to replace the conventional method, therefore to enhance the data capture speed about more than 10 times as that of conventional method, which implies to reach about 3000 dual-frame per second. The advantage is obvious from provide much accurate velocity measurement with good quality of concentration distribution.

The method may also be extended to other specific application that only part of sensing domain is interested.

Commentary on Sub-Section 3

Referring now to sub-section 3 above, this is a further description of tomography apparatus and methods embodying the invention, containing further information on how the partial tomogram (e.g. a band of pixels generally across a diameter of the sample cross section) can be calculated in embodiments of the invention from a reduced set of tomography measurements.

FURTHER DESCRIPTION

Further information regarding techniques for generating tomograms from 4-terminal measurements which may be used in certain embodiments of the present invention can be found in the following documents, the contents of each of which are incorporated herein by reference:

"A sensitivity coefficient method for the reconstruction of electrical impedance tomograms", C. J. Kotre, Clin. Phys. Physiol. Meas., 1989, Vol. 10, No. 3, 275-281

"EIT image reconstruction using sensitivity weighted filtered back projection", C. J. Kotre, Physiol. Meas. 15 (1994) A125-A136

"Inverse solutions for electrical impedance tomography based on conjugate gradients methods", M Wang, Meas, Sci. Technol., IOP, 13 (2002) 101-117

Further useful background information to the invention can be found in the following 4 papers, the contents of each of which are also incorporated herein by reference:

1. Brown, B. H. and Barber, D. C. (1985) *Tomography*, UK Patent No. GB2160323A.
2. Brown, B. H. and Seagar, A. D. (1987) 'The Sheffield data collection system', *Clin. Phys. Physiol. Meas.* 8 (Suppl. A), 91-97.
3. Wang, M. and Yin, W. (2002) '*Electrical impedance tomography*', PCT/GB01/05636, GB0129772.9, EP1347706, U.S. Pat. No. 6,940,286, Publication Number WO 02/053029
4. Wang, M., Dickin, F. and Williams, R. (1995) '*Electrical impedance tomography*', PCT/GB95/00520, GB2300927, AU18570/95, EP749285, U.S. Pat. No. 5,807,251, Publication number WO 95/24155

It will be appreciated that certain aspects of the invention aim to provide fast and simple operation in both the hardware data collection and imaging reconstruction, focusing on partial domain. Certain aspects provide:

1. Specific sensing or electrode operation procedure for the example of imaging along the diameter of pipeline
2. Pre-calculated sensitivity distribution on the pixels interested (e.g. four columns of pixels along the diameter of cross-section)
3. Only limited measurements are used for Image reconstructed with SBP method
4. ASI-special allocation of electrodes to highlight part region of interested Thus, certain embodiments of the invention may also utilise a pre-calculated sensitivity distribution for the array of pixels to be calculated from the reduced set of tomography measurements.

It will be appreciated that by employing techniques described above, in further embodiments of the invention any part of process domain can be imaged with limited measurements.

With the overlapping images from repetitions of the projection-measurement but with rotated angle (electrode), a full tomography image can be obtained.

Figure 17:
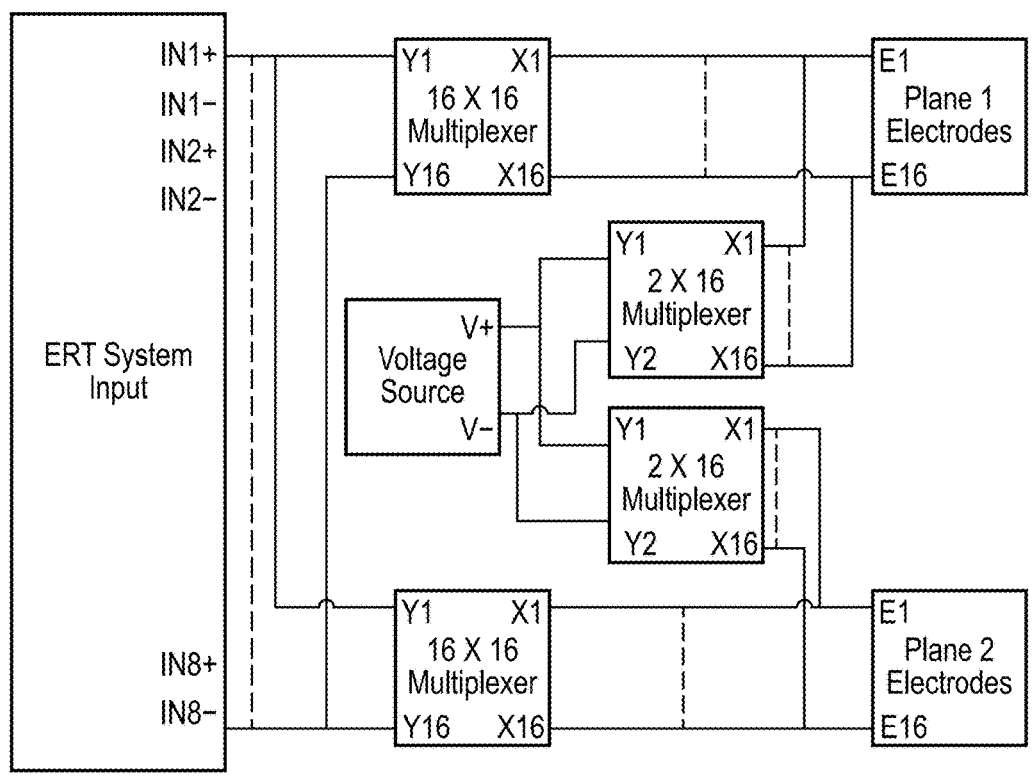
FIG. 17 illustrates an EIT system embodying the invention.

Referring now to FIG. 17, this shows an EIT system which may be used in embodiments of the invention (for example with PILM techniques) or with conventional EIT techniques. It is capable of 8 simultaneous measurements. Further modifications can also be made to use 16×16 multiplexer arrays such that any electrode can be chosen for measurement at any time. Similarly, the excitation source signals can also be connected to any electrode using multiplexers. By controlling the multiplexers, a maximum of 8 differential signals can be selected at a time. Therefore a full frame of 16 electrode adjacent measurement can be obtained by switching between the electrodes 4 times. This flexibility will facilitate implementation of PILM. The specific measurement signals of PILM can be chosen easily using this design thereby dramatically increasing the measurement speed. Since any electrode can be chosen for measurement at any time, this design is also flexible for applying different measurement strategies. It will effectively provide a frame rate of 2500 dfps (dual-plane per second). For PILM, the speed can be increased to around 6000 dfps.

The invention claimed is:

1. A tomography apparatus comprising:
   a plurality of electrodes arranged around a perimeter of a cross section of a sample volume for containing a liquid or mixed-phase sample, each electrode being arranged to be in electrical contact with a sample contained in the sample volume;
   a measurement means adapted to perform a set of measurements, each measurement comprising driving a current between a first respective adjacent pair of said electrodes and measuring a voltage developed across a second respective adjacent pair of said electrodes; and
   a processing means adapted to generate a tomogram indicative of sample conductivity over said cross section from said set of measurements,
   wherein the processing means is arranged to calculate sample conductivity values of a portion of said cross section from said set of measurements and generate said tomogram from said calculated sample conductivity values of said portion using an assumption of symmetry.

2. The apparatus of claim 1, wherein said plurality of electrodes are distributed asymmetrically around said perimeter.

3. The apparatus of claim 2, wherein said portion is one half of said cross section, and the assumption of symmetry is that sample conductivity over the other half mirrors said one half.

4. The apparatus of claim 3, wherein the apparatus further comprises a cylindrical pipe, arranged with its longitudinal axis horizontal, arranged to contain a flowing sample, the sample volume being an interior volume of the pipe, and said cross section being a circular cross section of the pipe interior, in a vertical plane perpendicular to the longitudinal axis.

5. The apparatus of claim 2, wherein said portion is a radial portion extending from a centre of the cross section to the perimeter, and the assumption of symmetry is that sample conductivity over said cross section is a function of radius only.

6. The apparatus of claim 5, wherein the apparatus further comprises a cylindrical pipe, arranged with its longitudinal axis vertical, arranged to contain a flowing sample, the sample volume being an interior volume of the pipe, and said cross section being a circular cross section of the pipe interior, in a horizontal plane.

7. The apparatus of claim 2, wherein said plurality of electrodes consists of 8 electrodes, said perimeter is circular, and 6 of said 8 electrodes are distributed around one half of the perimeter, with the remaining 2 of said 8 electrodes being distributed around the other half of the perimeter.

8. The apparatus of claim 1 wherein said plurality of electrodes are distributed uniformly around said perimeter.

9. The apparatus of claim 8, wherein said portion extends across the cross section from one side of the perimeter to an opposite side of the perimeter and includes a centre of the cross section.

10. The apparatus of claim 9, wherein said portion is a band extending diametrically across the cross section.

11. The apparatus of claim 9, wherein said portion consists of a plurality of rows of pixels, each row extending across the cross section, and the rows being parallel to one another.

12. The apparatus of claim 9, wherein said portion consists of a single row of pixels extending across the cross section, along a diameter of the cross section.

13. The apparatus of claim 8, wherein the apparatus further comprises a cylindrical pipe, arranged with its longitudinal axis vertical, arranged to contain a flowing sample, the sample volume being an interior volume of the pipe, and said cross section being a circular cross section of the pipe interior, in a horizontal plane.

14. The apparatus of claim 13, wherein the assumption of symmetry is that sample conductivity over said cross section is a function of radius only.

15. The apparatus of claim 8, wherein said perimeter is circular and said set of measurements comprises a first sub-set and a second sub-set, each of the first sub-set of measurements comprising driving a current between a respective pair of adjacent electrodes and measuring a voltage developed across a diametrically opposite pair of electrodes, and each of the second sub-set of measurements comprises driving a current between a respective pair of adjacent electrodes and measuring a voltage developed across an opposite respective pair of electrodes along a respective chord of the circular perimeter, wherein the chords of the second sub-set of measurements are parallel to one another.

16. The apparatus of claim 15, wherein the set of measurements consists of the first sub-set, the second sub-set, and a third sub-set, wherein the third subset comprises a plurality of measurements using respective pairs of electrodes at opposite ends of chords extending across the perimeter in a direction at least substantially perpendicular to the chords of the second sub-set.

17. The apparatus of claim 16, wherein the third sub-set further comprises a plurality of measurements using respective pairs of electrodes at opposite ends of further chords extending across the perimeter.

18. A flow measurement or monitoring apparatus comprising the tomography apparatus of claim 1.

19. A tomography method comprising:
   arranging a plurality of electrodes around a perimeter of a cross section of a sample volume for containing a liquid or mixed-phase sample, each electrode being arranged to be in electrical contact with a sample contained in the sample volume;
   performing a set of measurements, each measurement comprising driving a current between a first respective adjacent pair of said electrodes and measuring a voltage developed across a second respective adjacent pair of said electrodes; and
   generating a tomogram indicative of sample conductivity over said cross section from said set of measurements,
   wherein the method further comprises calculating sample conductivity values of a portion of said cross section from said set of measurements and generating said tomogram from said calculated sample conductivity values of said portion using an assumption of symmetry.

* * * * *